US011389386B2

(12) United States Patent
Loy et al.

(10) Patent No.: US 11,389,386 B2
(45) Date of Patent: Jul. 19, 2022

(54) PHOTOCHEMICALLY STABLE, NON-LEACHING, BRIDGED POLYSILSESQUIOXANE BASED SUNSCREENS

(71) Applicant: ARIZONA BOARD OF REGENTS ON BEHALF OF THE UNIVERSITY OF ARIZONA, Tucson, AZ (US)

(72) Inventors: Douglas A. Loy, Tucson, AZ (US); Stephanie H. Tolbert, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 16/074,043

(22) PCT Filed: Jan. 30, 2017

(86) PCT No.: PCT/US2017/015588
§ 371 (c)(1),
(2) Date: Jul. 30, 2018

(87) PCT Pub. No.: WO2017/132655
PCT Pub. Date: Aug. 3, 2017

(65) Prior Publication Data
US 2019/0038537 A1 Feb. 7, 2019

Related U.S. Application Data

(60) Provisional application No. 62/288,795, filed on Jan. 29, 2016.

(51) Int. Cl.
A61K 8/58 (2006.01)
C01B 33/12 (2006.01)
C01B 33/18 (2006.01)
A61K 8/02 (2006.01)
A61Q 17/04 (2006.01)
C09C 1/30 (2006.01)

(52) U.S. Cl.
CPC .......... *A61K 8/585* (2013.01); *A61K 8/025* (2013.01); *A61Q 17/04* (2013.01); *C01B 33/12* (2013.01); *C01B 33/18* (2013.01); *A61K 2800/412* (2013.01); *A61K 2800/413* (2013.01); *A61K 2800/43* (2013.01); *A61K 2800/95* (2013.01); *C01P 2002/84* (2013.01); *C01P 2002/85* (2013.01); *C01P 2004/03* (2013.01); *C01P 2004/04* (2013.01); *C01P 2004/32* (2013.01); *C01P 2004/51* (2013.01); *C01P 2004/52* (2013.01); *C09C 1/3063* (2013.01)

(58) Field of Classification Search
CPC ......... A61K 8/585; C01B 33/18; A61Q 17/04
See application file for complete search history.

(56) References Cited

U.S. PATENT DOCUMENTS

| 3,317,473 | A | 5/1967 | Ploeger et al. |
| 4,446,262 | A | 5/1984 | Okumura et al. |
| 2006/0069191 | A1 | 3/2006 | Durairaj et al. |
| 2009/0324654 | A1 | 12/2009 | Polonka et al. |
| 2010/0003204 | A1 | 1/2010 | Loy et al. |
| 2010/0059433 | A1 | 3/2010 | Freeman et al. |
| 2010/0119464 | A1 | 5/2010 | Gaudry et al. |
| 2012/0017503 | A1 | 1/2012 | Riggs et al. |

OTHER PUBLICATIONS

Datz, S. et al. "Lipid bilayer-coated curcumin-based mesoporous organosilica nanoparticles for cellular delivery" Microporous and Mesoporous Materials 225 (2016) 371-377 (Year: 2016).*
Hesemann, P. et al. "Novel silica-based hybrid materials incorporating binaphthyl units: a chiral matrix effect in heterogeneous asymmetric catalysis" Tetrahedron: Asymmetry 11 (2000) 2183-2194 (Year: 2000).*
Kidsaneepoiboon, P. et al. "Organic-inorganic hybrid polysilsesquioxane nanospheres as UVA/UVB absorber and fragrance carrier" J. Mater. Chem., 2011, 21, 7922 (Year: 2011).*
Sundaryono, A. et al. "Attempt to protect wood using copper(II) complex with 1,7-diphenyl-1,6-heptadiene-3,5-dione, a non-phenolic curcuminoid" Holz als Roh- und Werkstoff 61 (2003) 377-381 (Year: 2003).*
Walenzyk, T. et al. "Synthesis of mono-dispersed spherical silica particles containing covalently bonded chromophores" International Journal of Cosmetic Science, 2005, 27, 177-189 (Year: 2005).*
Patani, G.A. et al. "Bioisosterism: A Rational Approach in Drug Design" Chem. Rev. 1996, 96, 3147-3176 (Year: 1996).*
Casiraghi G., et al. "Selective step-growth phenol-aldehyde polymerization. 3. Synthesis. characterization. and x-ray analysis of regular all-ortho ethylidene-linked oligonuclear phenolic compounds", Macromolecules 1984 vol. 17. Issue 1. pp. 19-28.
Muylaert I., et al. "Ordered mesoporous phenolic resins: Highly versatile and ultra stable support materials". Advances in Colloid and Interface Science. 2012. vol. 175, pp. 39-51.

(Continued)

*Primary Examiner* — Andrew S Rosenthal
(74) *Attorney, Agent, or Firm* — Nguyen Tarbet LLC

(57) ABSTRACT

Bridged polysilsesquioxane based sunscreens prepared as nanoparticles via oil/water microemulsion polymerization, sol-gel polymerizations, or a modified Stober process. Minimized leaching and decreased levels of photo-degradation were achieved with covalent incorporation, with bridged incorporation necessary to ensure isolation of the sunscreen and any photo-products from skin. SPF values of were found to be comparable to existing commercial sunscreens. Furthermore the bridged polysilsesquioxane based sunscreens can be classified as broad-spectrum, and rate from moderate to superior in terms of UVA protective ability.

10 Claims, 12 Drawing Sheets

(9 of 12 Drawing Sheet(s) Filed in Color)

(56) References Cited

OTHER PUBLICATIONS

International Search Report for PCT Application No. PCT/US17/41564 dated Jul. 10, 2017.
International Search Report for PCT Application No. PCT/US17/15588 dated Apr. 12, 2017.
Tolbert, SH et al., New Hybrid Organic/Inorganic Polysilsesquioxane-Silica Particles as—Sunscreens, ACS Applied Materials & Interfaces 8, pp. 3160-3174, Jan. 5, 2016.
Riccio, DA et al., Stober Synthesis of Nitric Oxide-Releasing S-Nitrosothiol-Modified Silica Particles, Chemical Materials 23(7), pp. 1-23 (pp. 1727-1735), 2011.

* cited by examiner

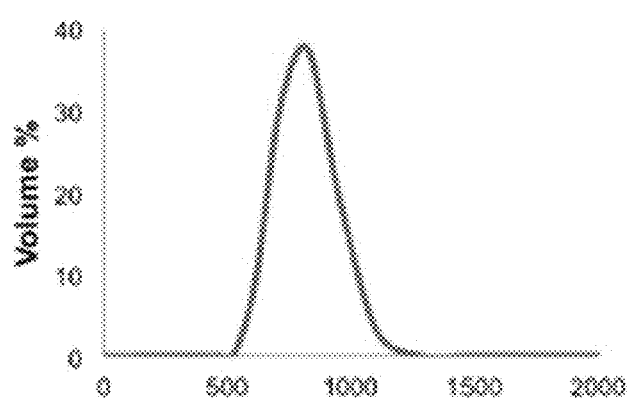
FIG. 2A
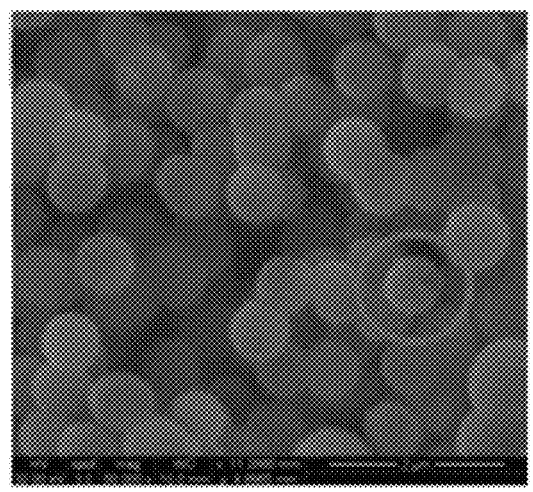
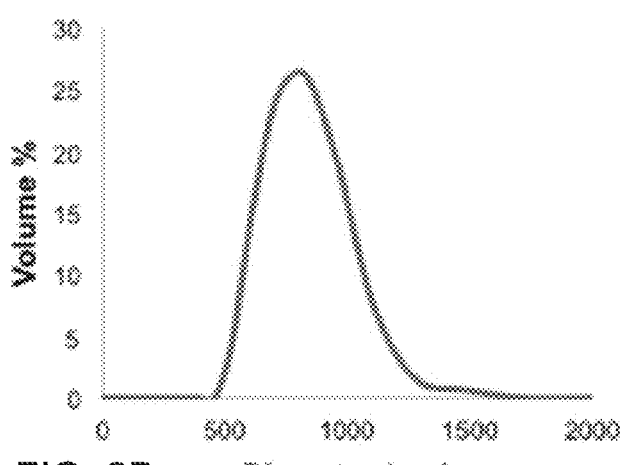
FIG. 2B
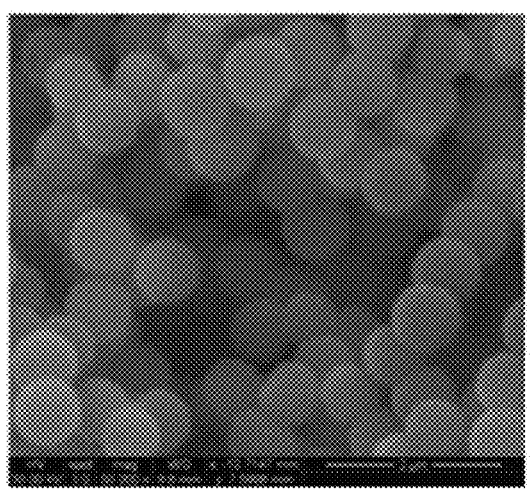
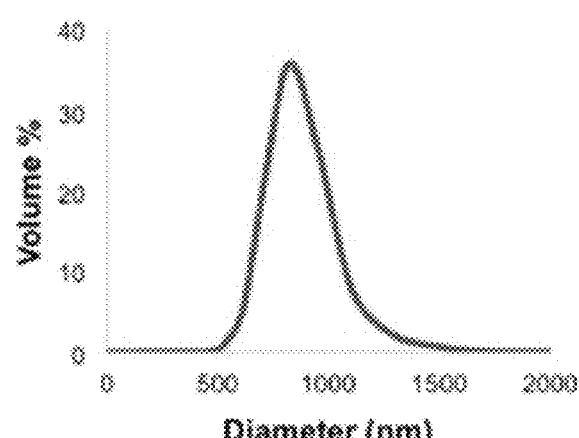
FIG. 2C
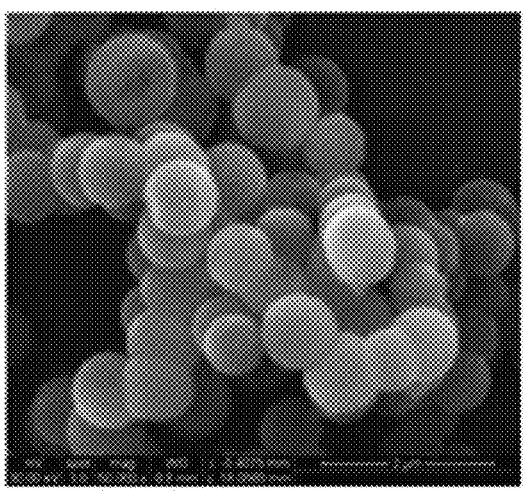

PHOTOCHEMICALLY STABLE, NON-LEACHING, BRIDGED POLYSILSESQUIOXANE BASED SUNSCREENS

CROSS REFERENCE

This application is a 371 of PCT/US2017/015588 filed Jan. 30, 2017, which claims priority to U.S. Patent Application No. 62/288,795, filed Jan. 29, 2016, the specification(s) of which is/are incorporated herein in their entirety by reference.

FIELD OF THE INVENTION

The present invention relates to sunscreens, in particular, to sunscreens based on nanoparticles of bridged polysilsesquioxanes.

BACKGROUND OF THE INVENTION

UV radiation (100-400 nm) represents ~10% of electromagnetic radiation (sunlight) that reaches the Earth's surface, and can be separated into three main types: UVC (100-290 nm), which has the shortest wavelength and highest energy; UVB (290-320 nm); and UVA (320-400 nm), which has the longest wavelength and lowest energy. UVA is further divided into UVA-I (340-400 nm) and UVA-II (320-340 nm). In small doses, UV radiation can be beneficial for vitamin D production or as therapeutic treatment for skin disorders, but too much exposure can cause several harmful photo-biological effects such as erythema (sunburn); accelerated skin ageing resulting in a variety of visible effects such as pronounced deep furrows, sagging, wrinkles, uneven pigmentation, dryness, and a leathery appearance; and most alarming, skin cancer. In the case of the latter, exposure accounts for the development of approximately 90% of all non-melanoma carcinomas according to the Environmental Protection Agency (EPA), with an estimated 3.5 million+ new cases of basal and squamous cell carcinoma diagnosed in the United States each year.

UVB has traditionally been thought to be the most harmful radiation to skin, and the prevalence of UVB absorbing active ingredients in commercial sunscreens has reflected this belief. Recent studies, however, have detailed the harmful effects of UVA exposure as well, for sufficient doses of UVA, particularly UVA-II, can in fact induce sunburn. While the sunburn potential of UVA is less than that of UVB, exposure to lower energy UVA over a prolonged period will result in the same degree of sunburn as exposure to higher energy UVB for a shorter period of time.

Alterations to the elastic fibers, termed elastosis, is characterized by hyperplasia (increase in cell proliferation), causing the fibers to thicken, degrade and accumulate. Eventually, they degenerate into an amorphous mass and become granular in appearance. Substantial loss of collagen is also seen in response to extensive UV exposure, for it is replaced by the accumulated fibers from elastosis. Elastosis can be induced by both UVB and UVA radiation. Due to the deeper penetration depth of UVA in skin), increased absorption of UVA in persons protected with sunscreens that only filter UVB, and in turn extended hours in the sun without the warning of sunburn, UVA has been found to be the major contributor of accelerated skin aging. For this reason, commercial sunscreen formulations are increasingly including active ingredients to attenuate UVA radiation.

To mitigate UV exposure, the use of sunscreens, which contain active ingredients that block UV, is recommended. Organic absorber sunscreens provide protection by preventing the penetration of UV radiation into skin via absorption of high energy UV, at which point they undergo transitions from the ground state to a higher energy state that correspond to the energy of radiation absorbed. This absorption is mediated by emission of lower energy radiation in the form of isomerization, visible light (fluorescence), or infrared (heat) back to the ground state. Compounds that fit these criteria are divided into several structural classes including p-aminobenzoic acid and analogues (PABAs), salicylates, cinnamates, benzophenone, dibenzoylmethanes, and camphor derivatives among others. While these examples are successful at absorbing UV radiation, they are limited in safety and effectiveness over time due to UV-induced decomposition and photo-toxicity, as well as photo-allergenic effects. For example, salicylates are UVB absorbing sunscreens that can cause allergic reactions and skin inflammation. Sunscreen compounds are even known to systemically absorb into the body after topical application, leading to concerns about their estrogenicity. As a result, stabilization and isolation from skin has increasingly become necessary to ensure their continual use.

Instability and toxicity of organic absorber sunscreens is currently moderated by embedding within organic matrices such as gelatin, polymers, lipids, and cyclodextrins; as well as inorganic matrices such as silica ($SiO_2$), or alumina ($Al_2O_3$) to be dispersed in lotions or cosmetics. Incorporation within silica particles has increasingly become a popular method due to low stability of organic matrices upon UV irradiation. Thus, isolating sunscreen from skin via incorporation within silica particles can be beneficial to ameliorate the problems associated with sunscreens, such as photo-degradation in the presence of UV, leeching, and skin inflammation.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide for sunscreen compositions that have improved UV stability and UV protective ability, as well as minimal sunscreen leaching, as specified in the independent claims. Embodiments of the invention are given in the dependent claims. Embodiments of the present invention can be freely combined with each other if they are not mutually exclusive.

According to embodiments of the present inventions, the sunscreens based on nanoparticles of bridged polysilsesquioxanes were prepared and found to have superior photochemical stability to ultraviolet light compared to hollow silica particles containing liquid organic sunscreens or sunscreens with pendant polysilsesquioxanes. In one embodiment, bridged monomers with salicylate or curcuminoid sunscreens were prepared with trialkoxysilyl groups on either end of chromophores attached through hydrolytically stable Si—C bonds. The bridged monomers were polymerized or copolymerized with tetraalkoxysilane (such as tetramethoxysilane, or tetraethoxysilane), water glass or organotrialkoxysilane comonomers (such as methyltriethoxysilane) by modified Stöber, sol-gel or microemulsion polymerizations to afford particles about 50-500 nm in diameter. The particles were purified by centrifugation and/or filtered and were dried. The particles dispersed in ethanol, water, glycerol or oil could be applied as sunscreens to block ultraviolet light. As will be further described herein, SPF and other sunscreen protection factors were determined and found to be comparable to existing commercial sunscreens. Leaching studies showed that the bridged sunscreens had infinitesimal leaching; and photostability studies showed that the bridged sunscreens lasted longer and suffered less UV degradation than either physically encapsulated or pendant attached sunscreens.

In some embodiments, the monomers could be prepared with benzophenone, acetophenone, cinnamate and other chromophores between the trialkoxysilyl groups. In other embodiments, the UV absorbing bridged monomers could be prepared from any sunscreen molecule bearing with two or more hydroxyl groups, amine groups, or an amine and hydroxy through formation of urethane or urea linkages to the triethoxysilyl or trimethoxysilyl groups using isocyanatopropyltriethoxysilane or isocyanatopropyltrimethoxysilane. In further embodiments, the bridged sunscreens can be prepared by reacting the sunscreen molecule with the two or more hydroxyl or amine groups with the epoxide groups in two or more equivalents of glycidyloxypropyltrimethoxysilane or glycidyloxypropyltriethoxysilane. In yet further embodiments, the monomers could also be prepared from sunscreen molecules with carboxylic acid groups by forming amide linkages with aminopropyltriethoxysilane or aminopropyltrimethoxysilane.

In one embodiment, the present invention features a sunscreen composition comprising one or more monomers of a bridged compound according to Formula I:

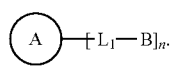

Formula I

In one embodiment, A is a UV absorbing moiety, B is a trialkoxysilyl group, n is at least 2 (i.e. n is 2 or 3), and $L_1$ is a linker group according to Formula II, III, or IV:

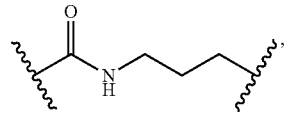

Formula II

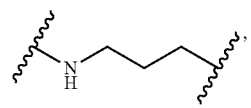

Formula III

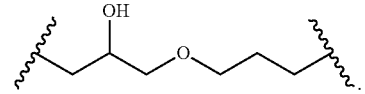

Formula IV

Preferably, $L_1$ is covalently bonded to A to effectively prevent leeching of A from the sunscreen composition. The bridged compound monomers can be polymerized to form bridged polysilsesquioxane-based sunscreen particles. The sunscreen composition may be resistant to photo-degradation.

In another embodiment, the present invention features a sunscreen formulation comprising any of the sunscreen compositions described herein, a cosmeceutically-acceptable sunscreen carrier comprising at least one solubilizer and at least one cosmetic adjuvant such as, for example, preservatives, antifoams, perfumes, oils, waxes, propellants, dyes, pigments, film-forming and waterproofing agents, emulsifiers, surfactants, thickeners, binders, humectants, exfoliants and emollients. Preferably, the sunscreen composition is present in an amount effective to absorb UV radiation.

According to another embodiment, the present invention features a sunscreen formulation comprising any of the sunscreen compositions described herein, and a pharmaceutically-acceptable sunscreen carrier. Preferably, the sunscreen composition is present in an amount effective to absorb UV radiation.

In another embodiment, the present invention features a method of protecting a skin of a mammal from harmful photo-biological effects of UV radiation. The method may comprise topically applying to the skin of the mammal an effective coating of a sunscreen formulation comprising any of the sunscreen composition described herein.

In yet another embodiment, the present invention features a method for preventing leeching of a UV absorbing compound. The method may comprise providing a plurality of monomers of the UV absorbing compound, covalently bonding at least two trialkoxysilanes to each monomer of the UV absorbing compound, thereby forming a bridged compound monomer, and polymerizing the bridged compound monomers to form a bridged polysilsesquioxane-based sunscreen particle. Without wishing to limit the invention to a particular theory or mechanism, the covalent bonding of the at least two trialkoxysilanes to the UV absorbing compound can be effective for preventing leeching of the UV absorbing compound from the sunscreen particle. Moreover, the sunscreen particle can be resistant to photo-degradation In a further embodiment, the present invention features a method of producing a bridged polysilsesquioxane-based sunscreen particle for use in a sunscreen formulation. The method may comprise providing a plurality of monomers of a UV absorbing compound, covalently bonding at least two trialkoxysilanes to each monomer of the UV absorbing compound, thereby forming a bridged compound monomer, and polymerizing the bridged compound monomers to form a bridged polysilsesquioxane-based sunscreen particle. Without wishing to limit the invention to a particular theory or mechanism, the covalent bonding of the at least two trialkoxysilanes to the UV absorbing compound is effective for preventing leeching of the UV absorbing compound from the sunscreen particle. Moreover, the sunscreen particle may be resistant to photo-degradation.

BRIEF DESCRIPTION OF THE DRAWINGS

This patent application contains at least one drawing executed in color. Copies of this patent or patent application publication with color drawing(s) will be provided by the Office upon request and payment of the necessary fee. The features and advantages of the present invention will become apparent from a consideration of the following detailed description presented in connection with the accompanying drawings in which:

FIGS. 2A-2C show dynamic light scattering (DLS) plots and scanning electron micrographs (SEM's) of particles prepared via microemulsion polymerizations. FIG. 2A depicts physically encapsulated salicylate particles (E-Sal), FIG. 2B depicts hollow silica particles made without sunscreen, and FIG. 2C depicts E-Sal with capping (Cap E-Sal). An example of shell rupturing is circled in red. DLS data represents the average of three trials. Diameters of 743±78 nm and 761±57 nm were seen in FIGS. 2A and 1B according to SEM.

DESCRIPTION OF PREFERRED EMBODIMENTS

Figure 1:
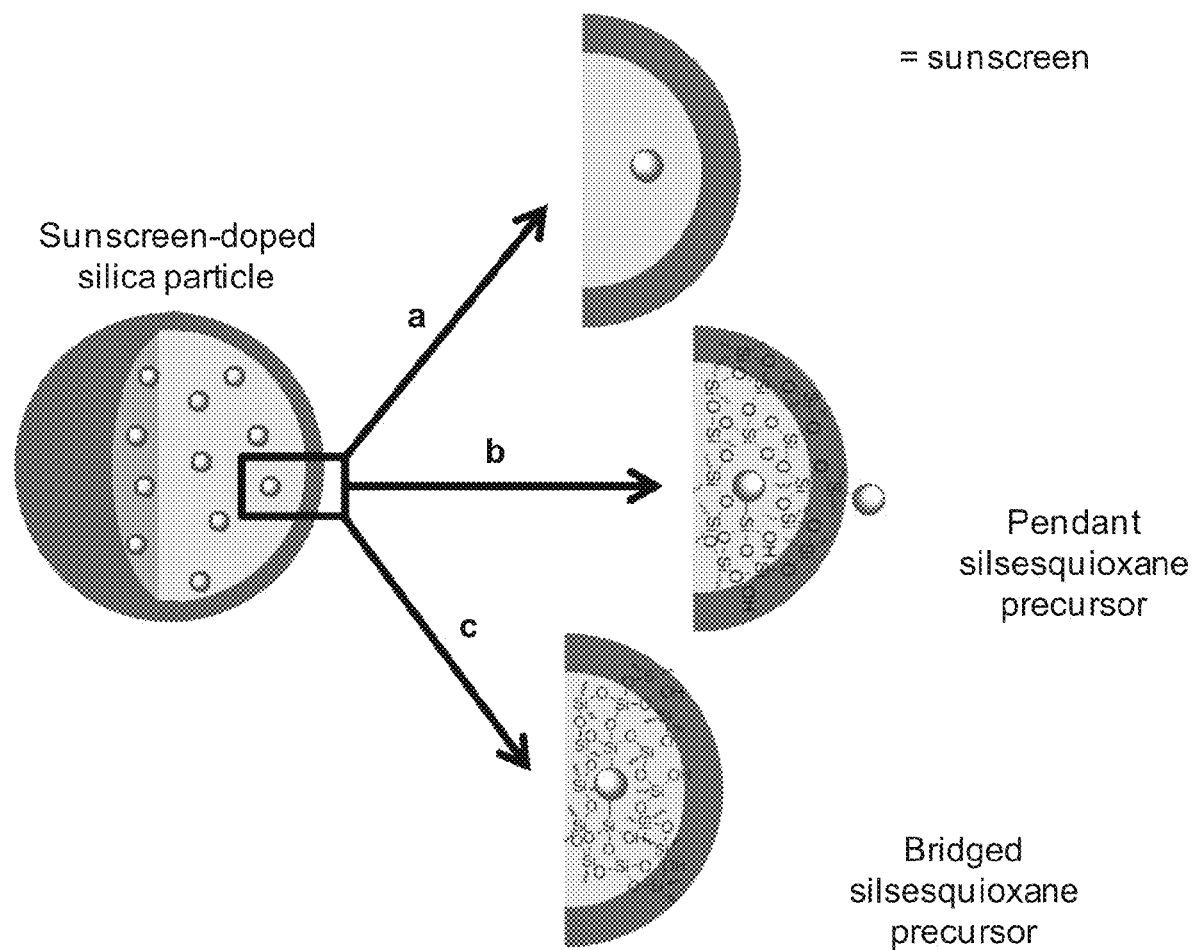
FIG. 1 is an illustration of the methods of sunscreen incorporation within spherical silica particles, where a shows physically encapsulated sunscreen particles (non-covalent), b shows pendant-covalent sunscreen particles with a pendant silsesquioxane precursor, and c shows bridged-covalent sunscreen particles with a bridged silsesquioxane precursor.

As used herein, the efficacy of UVB-absorbing sunscreens is typically expressed as the sun protection factor (SPF), which compares the minimum UV dosage (MED, or minimum erythema) dose) necessary to produce a minimal perceptible erythemal response in skin with and without sunscreen protection, as shown below:

SPF=MED in sunscreen protected skin/MED in non-sunscreen protected skin Simply stated, SPF is a measure of how long a sunscreen remains effective at preventing the penetration of UVB radiation into the skin. To determine how long a sunscreen will be effective, a person can multiply the SPF factor by the length of time it takes him/her to burn without sunscreen protection. For instance, a person who develops a sunburn within 10 minutes when not wearing sunscreen can theoretically expect to be protected for 150 minutes when wearing a sunscreen of SPF 15.

As used herein, the UV absorbing moiety can be any dye that absorbs UV or any organic absorber that includes p-aminobenzoic acid and analogues (PABAs), salicylates, cinnamates, benzophenones, anthranilates, dibenzoylmethanes, and camphor derivatives, among others. Table A shows common organic UV absorbers and their structure and UV properties.

TABLE A

Common organic absorber structural classes, commercial examples, their chemical structure, and their UV absorption properties.

| Structural class | Commercial example | Chemical structure | $\lambda_{max}$ (nm) | Absorber Type | Molar extinction coefficient ($M^{-1}$ $cm^{-1}$) |
|---|---|---|---|---|---|
| PABA | Padimate O | 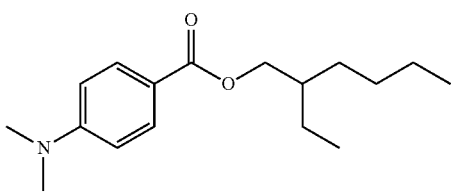 [SMILES: CCCCC(CC)COC(=O)c1ccc(N(C)C)cc1] | 289 | UVB | 28,400 |

TABLE A-continued

Common organic absorber structural classes, commercial examples,
their chemical structure, and their UV absorption properties.

| Structural class | Commercial example | Chemical structure | $\lambda_{max}$ (nm) | Absorber Type | Molar extinction coefficient ($M^{-1}$ $cm^{-1}$) |
|---|---|---|---|---|---|
| Salicylate | Octisalate | 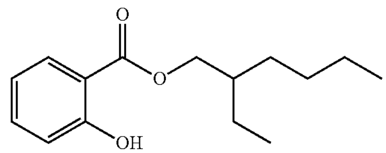 [SMILES: CCCCC(CC)COC(=O)c1ccccc1O] | 306 | UVB | 4,900 |
| Cinnamate | Octinoxate | 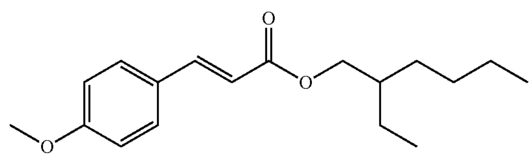 [SMILES: CCCCC(CC)COC(=O)/C=C/c1ccc(OC)cc1] | 312 | UVB | 24,200 |
| Benzophenone | Oxybenzone | 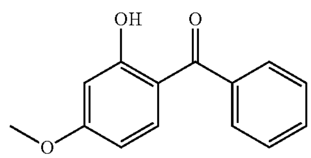 [SMILES: COc1ccc(C(=O)c2ccccc2)c(O)c1] | 288, 350 | UVB, UVA-II | 9,300 |
| Anthranilate | Meradimate | 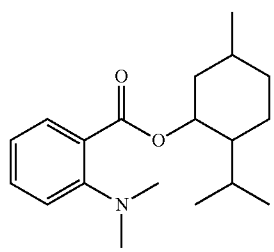 [SMILES: CC1CCC(C(C)C)C(OC(=O)c2ccccc2N(C)C)C1] | 336 | UVA | 5,600 |
| Dibenzoyl-methane | Avobenzone | 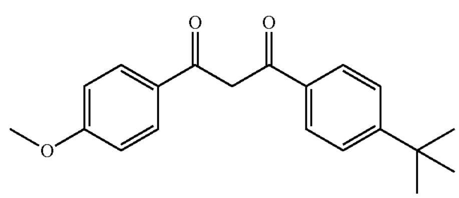 [SMILES: COc1ccc(C(=O)CC(=O)c2ccc(C(C)(C)C)cc2)cc1] | 360 | UVA | 31,000 |
| Camphor | Ecamsule | 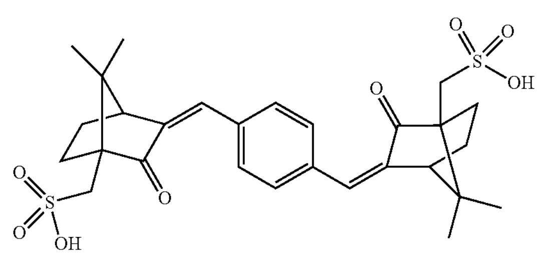 [SMILES: CC1(C)C2CCC1(CS(=O)(=O)O)C(=O)/C2=C\c1ccc(/C=C2\C(=O)C3(CS(=O)(=O)O)CCC2C3(C)C)cc1] | 345 | UVA | 47,000 |

Salicylates are o-hydroxy benzoates derived from the parent salicylic acid structure. Due to the ortho orientation of the hydroxy and carboxylate ester around the benzene ring, salicylates can undergo intramolecular hydrogen bonding which allows for UVB absorbance at ~300 nm due to lowered excitation energy. To compensate for the steric strain that arises from this ortho configuration, the hydroxy and carboxylate ester groups deviate slightly from planarity, and this lack of symmetry contributes to a low molar extinction coefficient. The two most common salicylates used as sunscreens are octisalate (2-ethylhexyl salicylate), and homosalate (homomenthyl salicylate). Other examples of salicylates include benzyl salicylate, homosalate, amal salicylate, triethanolamine salicylate, potassium salicyate, octisalate, p-isopropyl phenyl salicylate, and p-isopropyl benzyl salicylate.

Cinnamates are UVB absorbers, most notably octinoxate (2-ethylhexyl methoxycinnamate). Due to the site of unsaturation conjugated to both the aromatic ring and the carbonyl group, electronic delocalization can occur, the energy of which corresponds to wavelengths of 305-312 nm. Examples of cinnamates for use in sunscreens include potassium cinnamate, octyl cinnamate, ethyl-4-isopropyl cinnamate, ethyl-2,4-isopropyl cinnamate, methyl-2,4-isopropyl cinnamate, potassium p-methoxy cinnamate, sodium p-methoxy cinnamate, diethanolamine-p-methoxy cinnamate, propyl-p-methoxy cinnamate, isopropyl-p-methoxy cinnamate, isoamyl-p-methoxy cinnamate, octinoxate (2-ethylhexyl-p-methoxy cinnamate), cinoxate (2-ethoxyl-hexyl-p-methoxy cinnamate), cyclohexyl-p-methoxy cinnamate, hexyl-α-cyano-p-methoxy cinnamate, ethyl-α-cyano-β-phenyl cinnamate, and ethylhexyl-α-cyano-β-phenyl cinnamate.

Benzophenones are aromatic ketones that exhibit their UVB absorbing properties via resonance delocalization, which is aided by the presence of an electron-donating group in the ortho and/or para position. Aromatic ketones resonate more easily than the PABA, salicylate and cinnamate esters mentioned previously, ensuring a lower amount of energy and in turn a longer wavelength (>320 nm) is required for this transition. Examples of benzophenones for use as sunscreens include oxybenzone, sulisobenzone, dioxybensone, mexenone, and 2-ethylhexul-2-(4-phenyl benzoyl)benzoate.

Anthranilates are structurally similar to salicylates in that they contain an electron-donating group (in this case an amine) situated ortho to a carboxylate ester around the benzene ring. Intramolecular hydrogen bonding and electronic delocalization that arises from this orientation allows for UVA absorbance at ~330 nm. As with salicylates, anthranilates display a lower molar extinction coefficient (~5000 M-1 cm-1) than their para analogues (PABAs) due to the "ortho effect". Anthranilates for use as sunscreens are menthylanthranilate and homomenthyl-n-acetyl anthranilate.

Dibenzoylmethanes can absorb in the UVA region. They display their UV absorbing properties due to a keto/enol tautomerism, with the enol form being most stable due to intramolecular hydrogen bonding when the functional group in the 2-position on the first aromatic ring is a hydrogen. When the functional group is a hydroxy group, the keto form predominates. The keto form absorbs maximally at ~260 nm (UVC), while the enol form has $\lambda_{max}$ values exceeding ~345 nm, making them suitable UVA absorbers. Dibenzoylmethanes for use as sunscreens include butyl methoxydibenzoylmethane (avobenzone), 4-Isopropyldibenzoylmethane (Eusolex 8020), and 4,4'-Bis-methoxydibenzoylmethane (dianisoylmethane).

Camphors are bicyclic compounds that generally absorb in the UVB range (290-300 nm) and display a high molar extinction coefficient (generally >20,000 $M^{-1}$ $cm^{-1}$). Examples of camphor for use as sunscreens include 4-methylbenzylidene camphor (4-MBC), and ecamsule.

Bemotrizinol (Tinosorb S) and bisoctrizole (Tinosorb M) are broad-spectrum UV absorbers, and are highly photostable with minimal skin penetration and no known estrogenic effects in vitro. Additionally, they are known to stabilize other ingredients that are prone to photo-degradation, such as avobenzone and octinoxate. Bemotrizinol and bisoctrizole can be used as sunscreens in accordance with the present invention.

Curcumin is composed of a mixture of isomers that contain an average of two methyl esters and two phenol hydroxyl groups. Topical application of curcumin has been found to significantly reduce thymine dimerization in response to UVB radiation. Tetrahydrocurcumin is a non-pigmented derivative of curcumin.

As used herein, bridged-covalent incorporation involves the use of active ingredients that have been modified to contain two or more branching sites, with the UV absorbing species effectively "bridged" between them. These compounds are termed bridged silsesquioxanes. Without wishing to limit the invention to a particular theory or mechanism, since the minimum number of possible attachment sites is increased to six, bridged incorporation will display minimized leaching over that of physical and pendant counterparts due to more bonds being required to break. Additionally, the nature of the bridged silsesquioxane structure ensures the sunscreen ingredient is more than likely dispersed throughout the silica matrix as opposed to on the surface, and is more rigidly contained than the physical and pendant counterparts. As such, enhanced UV stability can be afforded since the increased immobilization ensures minimal excited state interactions.

As used herein, one embodiment of organotrialkoxysilanes can be of the formula $(R'O)_3Si—R$, wherein R' can be a methyl or ethyl, and R can be a methyl, ethyl, propyl, butyl, phenyl, vinyl, allyl, chloromethyl, 2-chloroethyl, or hydroxymethyl. For instance, the organotrialkoxysilane can be a methyltriethoxysilane. In another embodiment, the organotrialkoxysilanes can be of the formula $(R'O)_3Si—R—Si(OR')_3$, wherein R' can be a methyl or ethyl, and R can be a 1,4-phenylene, 1,3-phenylene, 4,4'-biphenylene, methylene, 1,2-ethylene, 1,2-ethenylene, 1,3-propylene, 1,6-hexylene, 1,8-octylene, 1,10-decylene. It is to be understood that any appropriate organotrialkoxysilanes can be used in accordance with the present invention, and that the present invention is not limited to the examples of the organotrialkoxysilanes described herein.

Referring now to FIG. 1-10, the present invention features a sunscreen composition comprising one or more monomers of a bridged compound according to Formula I:

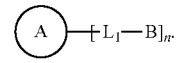

Formula I

In one embodiment, A is a UV absorbing moiety. B is a trialkoxysilyl group, n is at least 2, and $L_1$ is a linker group according to Formula II, III, or IV:

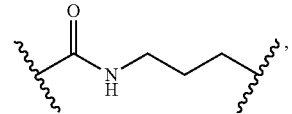

Formula II

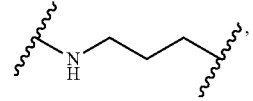

Formula III

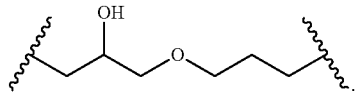

Formula IV

Preferably, $L_1$ is covalently bonded to A to effectively prevent leeching of A from the sunscreen composition. The bridged compound monomers can be polymerized to form bridged polysilsesquioxane-based sunscreen particles. Moreover, the sunscreen composition may be resistant to photo-degradation.

In some embodiments, A is selected from a group consisting of salicylate, curcuminoid, benzophenone, acetophenone, and cinnamate monomers. In other embodiments. A is an organic dye. In still other embodiment, A comprises at least two functional groups selected from a group consisting of a hydroxyl, an amine, and a carboxylic acid moiety. Preferably, $L_1$ is covalently bonded to the functional groups. In further embodiments, the trialkoxysilyl group may be a triethoxysilyl group or trimethoxysilyl group.

In another embodiment, the sunscreen composition may further comprise silicate comonomers in concentrations ranging from 0.001-95 mole %. Preferably, the silicate comonomers can copolymerized with the bridged compound monomers to form the bridged polysilsesquioxane-based sunscreen particles. The silicate comonomers may be selected from a group consisting of tetraalkoxysilane comonomers, sodium silicate comonomers, and organotrialkoxysilane comonomers. For example, the tetraalkoxysilane comonomers are selected from a group consisting of tetramethoxysilane comonomers and tetraethoxysilane comonomers.

In preferred embodiments, the sunscreen composition may be prepared by sol gel polymerization, microemulsion polymerization, or modified Stober polymerization. In some embodiments, the sunscreen particles may be irregularly spherical in shape. For instance, each sunscreen particle can have a mean diameter of about 50 to 750 nm.

According to another embodiment of the present invention, the sunscreen composition may comprise one or more monomers of a bridged compound according to Formula I:

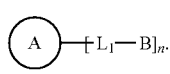

Formula I

Preferably, A is a UV absorbing moiety selected from a group consisting of salicylate, curcuminoid, benzophenone, acetophenone, and cinnamate. In one embodiment, B is a trialkoxysilyl group, n is 2 or 3, and $L_1$ is a linker group according to Formula II, III, or IV:

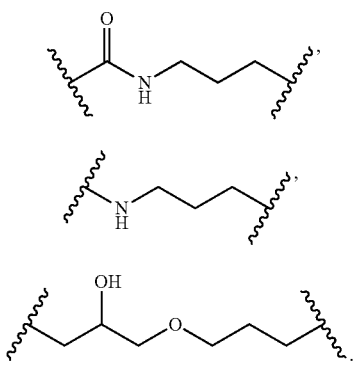

Formula II

Formula III

Formula IV

Preferably, $L_1$ is covalently bonded to a reactive functional group of A to effectively prevent leeching of A from the sunscreen composition. The value of n may be dependent on the reactive functional groups of A. In some embodiments, the trialkoxysilyl group may be a triethoxysilyl group or trimethoxysilyl group.

In preferred embodiments, the bridged compound monomers can be polymerized to form bridged polysilsesquioxane-based sunscreen particles. Moreover, the sunscreen composition may be resistant to photo-degradation. The technique of preparing the sunscreen particles may be sol gel polymerization, microemulsion polymerization, or modified Stöber polymerization. In some embodiments, each sunscreen particle can have a mean diameter of about 50 to 750 nm.

In another embodiment, the sunscreen composition may further comprise silicate comonomers in concentrations ranging from 0.001-95 mole %. Preferably, the silicate comonomers can copolymerize with the bridged compound monomers to form the bridged polysilsesquioxane-based sunscreen particles. The silicate comonomers may be selected from a group consisting of tetraalkoxysilane comonomers, sodium silicate comonomers, and organotrialkoxysilane comonomers. For example, the tetraalkoxysilane comonomers are selected from a group consisting of tetramethoxysilane comonomers and tetraethoxysilane comonomers.

In yet another embodiment, the present invention features a sunscreen formulation comprising any of the sunscreen compositions described herein, a cosmeceutically-acceptable sunscreen carrier comprising at least one solubilizer and at least one cosmetic adjuvant selected from the group consisting of preservatives, antifoams, perfumes, oils, waxes, propellants, dyes, pigments, film-forming and waterproofing agents, emulsifiers, surfactants, thickeners, binders, humectants, exfoliants and emollients. Preferably, the sunscreen composition is present in an amount effective to absorb UV radiation. In some embodiments, the sunscreen formulation is in a form suitable for topical application. Examples include, but are not limited to, creams, ointment, suspensions, powders, lotions, gels, solids, foams, emulsions, liquid dispersions, sprays and aerosols.

The sunscreen formulation may further comprise an anti-oxidant to aid in preventing or reducing erythema and boost SPF. Anti-oxidants can include, but are not limited to, natural polyphenols such as flavonoids (catechins), resveratrol, retinol; green tea extract, procyanidolic oligomers, vitamins C, vitamin E and other tocopherols, and natural oils such as rosemary, argan oil, and clove oil.

Solubilizers may be required to ensure adequate solubility of the sunscreen composition. Examples of sunscreen solubilizers, include, but are not limited to, solvents such as water, carrier oils such as castor oil, jojoba oil, cottonseed oil, peanut oil and sesame oil; vegetable oils, modified vegetable oils, alcohols, glycerin, butyloctyl salicylate, dimethyl capramide, diisobutyl adipate, etc.

In some embodiments, dispersing agents, emulsifiers or thickening agents in the sunscreen formulation can aid in applying a uniform layer of the sunscreen particle. Suitable dispersing agents for the sunscreen formulations include those useful for dispersing the hybrid organic/inorganic sunscreen particles in a water phase, an oil phase, or part of an emulsion.

Emulsifiers may be used to disperse the sunscreen composition of the formulation. Suitable emulsifiers include ethoxylated fatty acids, ethoxylated esters, ethoxylated ethers, ethoxylated alcohols, phosphated esters, polyoxyethylene fatty ether phosphates, fatty acid amides, acyl lactylates, soaps and mixtures thereof. Examples thereof include glycerol stearate, fatty alcohols such as stearyl alcohol, cetyl alcohol, cetearyl alcohol, cetearyl palmitate, lauryl myristate and isopropyl palmitate, dimethicone copolyol phosphate, lecithin, stearic acid, sugar emulsifiers such as sucrose ester and sorbitan ester, modified vegetable esters such as polyglyceryl-6 polyricinoleate, glyceryl oleate, phosphate esters such as castor oil, soy emulsifiers, vegetable and fermented gums, lanolin, botanical extracts, polyoxyethylene (8) stearate, myristyl ethoxy (3) myristate, polyoxyethylene (100) monostearate, lauric diethanolamide, stearic monoethanolamide, hydrogenated vegetable glycerides, sodium steroyl-2-lactylate and calcium stearoyl-2-lactylate, soaps such as sodium stearate and triethanolamine stearate, lanolin and its derivatives and components such as acetylated lanolin, lanolin alcohols and lanolin fatty acids, etc.

Preservatives may be used to protect sunscreen formulation against microbial growth. Examples thereof include, but are not limited to glucose oxidase, lactoperoxidase, parabens such methyl, ethyl, propyl and butyl esters of hydroxybenzoic acid, EDTA, methylisothiazolinone, imidazolidinyl ureas, etc.

Thickening agents may be used to increase the viscosity of the sunscreen formulations. Suitable thickening agents include carbomers, acrylate/acrylonitrile copolymers, carboxyvinyl polymers, xanthan gum and combinations of these.

The sunscreen formulation may optionally contain an ingredient which enhances the waterproof properties and can form a polymeric film, such as acacia gum, rosin, esters, shellac, polyglyceryl-10 pentastearate, behenyl alcohol, lanolin, soluble collagen, polysaccharide based materials such as natural hydrocolloids, microcrystalline cellulose, modified cellulose, corn starch, dimethicone copolyol phosphate, diisostearoyl trimethyolpropane siloxysilicate, chitosan, dimethicone, polyethylene, PVP/Eicosene copolymer, adipic acids/diethylene glycol/glycerine crosspolymer, polyvinylpyrrolidone/vinylacetate, etc.

Skin conditioning agents can include humectants, exfoliants and emollients. Humectants are intended for moisturizing, reducing scaling and stimulating the removal of built scale from the skin. Examples include, but are not limited to, polyhydric alcohols such as propylene glycol, dipropylene glycol, polypropylene glycol, polyethylene glycol, sorbitol, 2-pyrrolidone-5-carboxylate, hydroxypropyl sorbitol, hexylene glycol, ethoxydiglycol 1,3-butylene glycol, 1,2,6-hexanetriol, glycerin, ethoxylated glycerin, alkoxylated glucose, hexanetriol, propoxylated glycerin and mixtures thereof. Exfoliants may be selected from alpha-hydroxy carboxylic acids, beta hydroxycarboxylic acids and salts of these acids.

Suitable emollients include those agents known for softening the skin or hair, which may be selected from hydrocarbons, fatty acids, fatty alcohols and esters. Waxes such as petrolatum, ceresin wax, carnauba wax, beeswax, and castor wax may be suitable emollients. For instance, petrolatum is a common hydrocarbon type of emollient conditioning agent. Other hydrocarbons that may be employed include alkyl benzoate, mineral oil, polyolefins such as polydecene, and paraffins, such as isohexadecane. Fatty acids and alcohols typically have from about 10 to 30 carbon atoms. Examples include, but are not limited to, myristic, isostearic, hydroxystearic, oleic, linoleic, ricinoleic, behenic and erucic acids and alcohols. Ester emollients can include triglyceride esters, acetoglyceride esters, ethoxylated glycerides, alkyl esters of fatty acids, ether esters, polyhydric alcohol esters and wax esters. Additional emollients or hydrophobic agents include $C_{12}$ to $C_{15}$ alkyl benzoate, dioctyladipate, octyl stearate, octyldodecanol, hexyl laurate, octyldodecyl neopentanoate, cyclomethicone, dicapryl ether, dimethicone, phenyl trimethicone, isopropyl myristate, capriylidcapric glycerides, propylene glycol dicaprylate/dicaprate and decyl oleate.

In alternative embodiments, the sunscreen formulations may further contain inorganic sunscreen agents such as titanium dioxide and zinc oxide. In still other embodiments, the sunscreen formulation may further comprise plant extracts such as aloe vera, witch hazel, and cucumber. Further embodiments of the sunscreen formulation can include anti-aging and skin nutrifying ingredients such as retinoids, hydroquinone, alpha hydroxy acids, hyaluronic acids, vitamins A, B, C, and E, rose hip oil, tea extracts, co-enzyme Q10, collagen, elastin, plant extracts, soy isoflavones, etc. Other suitable ingredients that may be used in the sunscreen formulation include, but are not limited to, ethyl cellulose, polyvinyl alcohol, carboxymethyl cellulose, vegetable gums and clays, proteins and polypeptides, and an alkaline agent such as sodium hydroxide or potassium hydroxide to neutralize, if desired, part of the fatty acids or thickeners which may be present.

According to another embodiment, the present invention features a sunscreen formulation comprising any of the sunscreen compositions described herein, and a pharmaceutically-acceptable sunscreen carrier. Preferably, the sunscreen composition is present in an amount effective to absorb UV radiation. The sunscreen formulation contain pharmaceutically-acceptable sunscreen carriers selected as appropriate for the formulation desired. For example, it is possible to prepare sunscreen formulation of the present invention in the form of organic solvent solutions, aqueous emulsions, gels, or aerosol formulation.

As used herein, the term "cosmeceutically-acceptable sunscreen carrier" or "pharmaceutically-acceptable sunscreen carrier", means one or more substantially non-irritating compatible filler diluents which are suitable for topical application to the skin of a mammal, i.e. human. The term "compatible", as used herein, means that the components of the carrier must be capable of being comingled with the sunscreen composition, and with each other, in a manner such that there is no interaction which would substantially reduce the efficacy of the composition during use for protecting the skin from the harmful effects of UV radiation. Cosmeceutically-acceptable and pharmaceutically-acceptable sunscreen carriers must, of course, be of sufficiently high purity and sufficiently low toxicity to render them suitable for topical administration to the mammal. The sunscreen carriers useful in the formulation of the present invention include, for example, water, oils, fats, waxes, synthetic polymers, emulsifiers, surfactants, perfumes, dyes, and preservatives.

In another embodiment, the present invention features a method of protecting a skin of a mammal from harmful photo-biological effects of UV radiation. The method may comprise topically applying to the skin of the mammal an effective coating of a sunscreen formulation comprising any of the sunscreen composition described herein.

In yet another embodiment, the present invention features a method for preventing leeching of a UV absorbing compound. The method may comprise providing a plurality of monomers of the UV absorbing compound, covalently bonding at least two trialkoxysilanes to each monomer of the UV absorbing compound, thereby forming a bridged compound monomer, and polymerizing the bridged compound monomers to form a bridged polysilsesquioxane-based sunscreen particle. Preferably, the covalent bonding of the at least two trialkoxysilanes to the UV absorbing compound can be effective for preventing leeching of the UV absorbing compound from the sunscreen particle. Moreover, the sunscreen particle can be resistant to photo-degradation.

In some embodiments, the UV absorbing compound may be a salicylate, curcuminoid, benzophenone, acetophenone, and cinnamate. In other embodiments, the UV absorbing compound is an organic dye that absorbs UV radiation. In still other embodiments, the UV absorbing compound comprises at least two functional groups, such as, for example, a hydroxyl, an amine, or a carboxylic acid moiety.

In a preferred embodiment, the trialkoxysilane may be covalently bonded to the functional group. Examples of the trialkoxysilane include, but are not limited to, aminopropyltriethoxysilane, aminopropyltrimethoxysilane, isocyanatopropyltriethoxysilane, isocyanatopropyltrimethoxysilane, glycidyloxypropyltrimethoxysilane, and glycidyloxypropyltriethoxysilane.

In another embodiment, the step of polymerizing the bridged compound monomers can further comprise providing silicate comonomers in concentrations ranging from 0.001-95 mole %, and copolymerizing the silicate comonomers with the bridged compound monomers to form the bridged polysilsesquioxane-based sunscreen particles. In some embodiments, the silicate comonomers may be tetraalkoxysilane comonomers, sodium silicate comonomers, and organotrialkoxysilane comonomers. For instance, the tetraalkoxysilane comonomers may be tetramethoxysilane comonomers and/or tetraethoxysilane comonomers.

In some embodiments, the sunscreen particle is an irregular spherical particle. The irregular spherical particle can have a mean diameter of about 50 to 750 nm. Examples of techniques of polymerizing the bridged compound monomers include sol gel polymerization, microemulsion polymerization, and modified Stöber polymerization.

In a further embodiment, the present invention features a method of producing a bridged polysilsesquioxane-based sunscreen particle for use in a sunscreen formulation. The method may comprise providing a plurality of monomers of a UV absorbing compound, covalently bonding at least two trialkoxysilanes to each monomer of the UV absorbing compound, thereby forming a bridged compound monomer, and polymerizing the bridged compound monomers to form a bridged polysilsesquioxane-based sunscreen particle. Without wishing to limit the invention to a particular theory or mechanism, covalent bonding of the at least two trialkoxysilanes to the UV absorbing compound can prevent leeching of the UV absorbing compound from the sunscreen particle. Moreover, the sunscreen particle may be resistant to photo-degradation.

In some embodiments, the UV absorbing may be a salicylate, curcuminoid, benzophenone, acetophenone, and cinnamate. In other embodiments, the UV absorbing compound is an organic dye that absorbs UV radiation. In still other embodiments, the UV absorbing compound comprises at least two functional groups such as, for example, a hydroxyl, an amine, or a carboxylic acid moiety.

In an exemplary embodiment, the trialkoxysilane may be covalently bonded to the functional group. Non-limiting examples of the trialkoxysilane include aminopropyltriethoxysilane, aminopropyltrimethoxysilane, isocyanatopropyltriethoxysilane, isocyanatopropyltrimethoxysilane, glycidyloxypropyltrimethoxysilane, and glycidyloxypropyltriethoxysilane.

In another embodiment, the step of polymerizing the bridged compound monomers further comprises providing silicate comonomers in concentrations ranging from 0.001-95 mole %, and copolymerizing the silicate comonomers with the bridged compound monomers to form the bridged polysilsesquioxane-based sunscreen particles. The silicate comonomers may be tetraalkoxysilane comonomers, sodium silicate comonomers, and organotrialkoxysilane comonomers. For example, the tetraalkoxysilane comonomers can be tetramethoxysilane comonomers and/or tetraethoxysilane comonomers.

In some embodiments, the sunscreen particle is an irregular spherical particle. The irregular spherical particle can have a mean diameter of about 50 to 750 nm. Examples of techniques of polymerizing the bridged compound monomers include sol gel polymerization, microemulsion polymerization, and modified Stöber polymerization.

EXPERIMENTAL

The following section describes leaching, photochemical stability, and sunscreen performance of salicylate and curcumin sunscreens encapsulated in silica particles evaluated as a function of physical encapsulation (E-Sal), physical encapsulation with capping (Cap-E-Sal), covalent attachment of sunscreens to the silica particles as pendant (P-Sal) and as bridged monomers (B-Sal and B-Curc). It is understood the present invention is not limited by the examples described herein.

Figure 11:
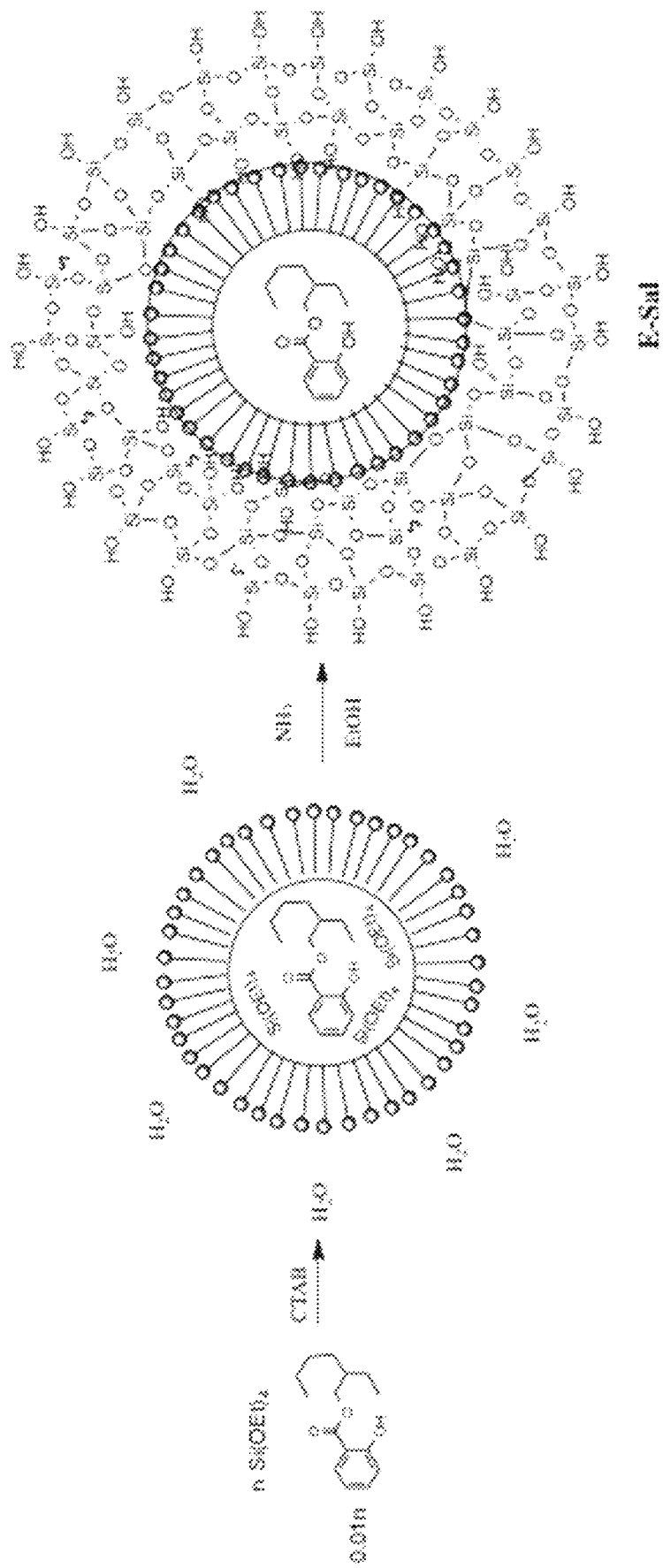
FIG. 11 shows a scheme of physical encapsulation of hydrophobic sunscreens using an oil-in-water microemulsion polymerization of tetraethoxysilane.

Sunscreens can be physically encapsulated in or covalently attached to silica particles. Hydrophobic sunscreens as the core of hollow silica particles can be prepared by oil-in-water (O/W) microemulsion polymerizations. As shown in FIG. 11, 2-Ethylhexyl salicylate was physically encapsulated in hollow silica particles (E-Sal) by O/W microemulsion polymerization of TEAS. Alternatively, water soluble sunscreens are encapsulated by a reverse microemulsion process (water-in-oil, or W/O). In both of these methods, inherent porosity or mechanical damage allow sunscreen to leak out.

Figure 12A:
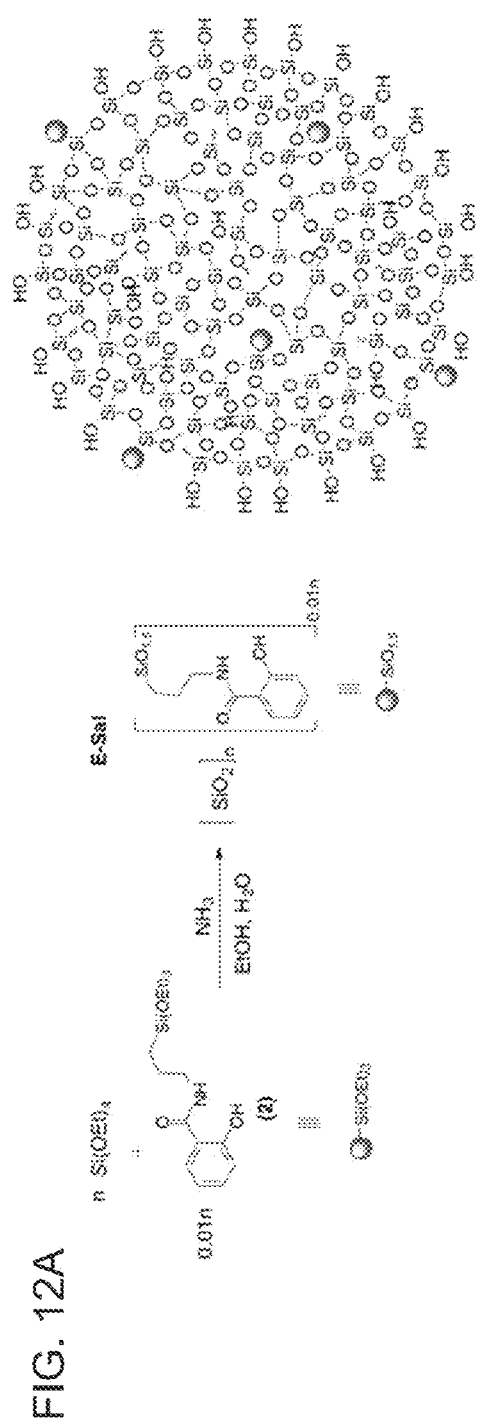
FIGS. 12A-12B show schemes of covalent encapsulation by copolymerization of sunscreen dyes bearing one (FIG. 12A) or two or more (FIG. 12B) triethoxysilyl groups with tetraethoxysilane in a sol-gel or Stöber polymerization.
Figure 12B:
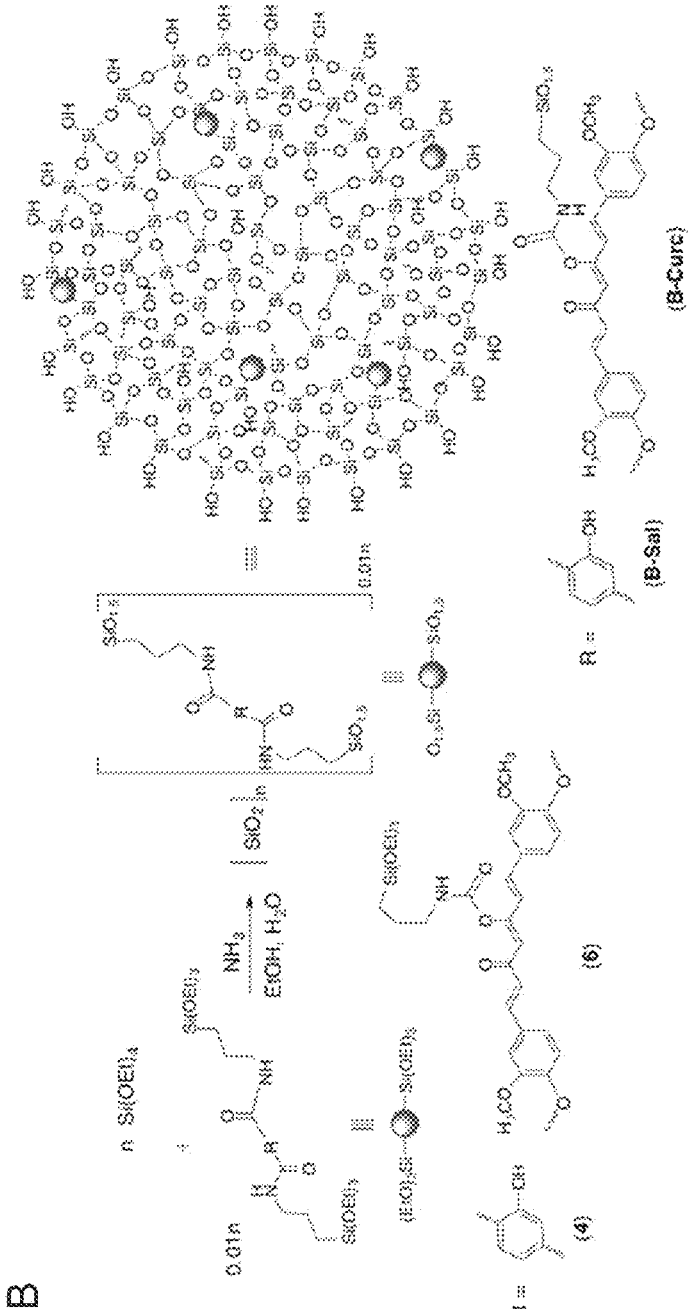

Covalent incorporation has increasingly superseded physical encapsulation as a means to minimize sunscreen leaching. In preferred embodiments of the present invention, sunscreens comprising hybrid organic-inorganic particles of this nature are prepared via sol-gel polymerization, most commonly by a modified Stober procedure. This method involves co-condensation of a silyl-modified organic monomer (organotrialkoxysilane) with a silica monomer, such as tetraethoxysilane (TEOS), in ammoniacal ethanol to afford a dilute suspension of organically modified silica particles. Sunscreen is less likely to leach from the silica matrix as it is attached to the silica particles via covalent bonds and, if in the interior of the particle, physical encapsulation. In addition, immobilization in the silica matrix decreases diffusion of reactive oxygen species and increases energy dissipation, thereby improving UV stability of organic sunscreens. As shown in FIGS. 12A-12B, covalent salicylate incorporation was achieved by Stöber polymerization of TEOS with salicylate monomer 2 with a single triethoxysilyl group (P-Sal, FIG. 12A) or 4 with two triethoxysilyl groups (B-Sal, FIG. 12B). Lastly, particles based on a second bridged sunscreen were prepared from curcuminoid 6 with three triethoxysilyl groups (B-Curc, FIG. 12B).

Figure 13:
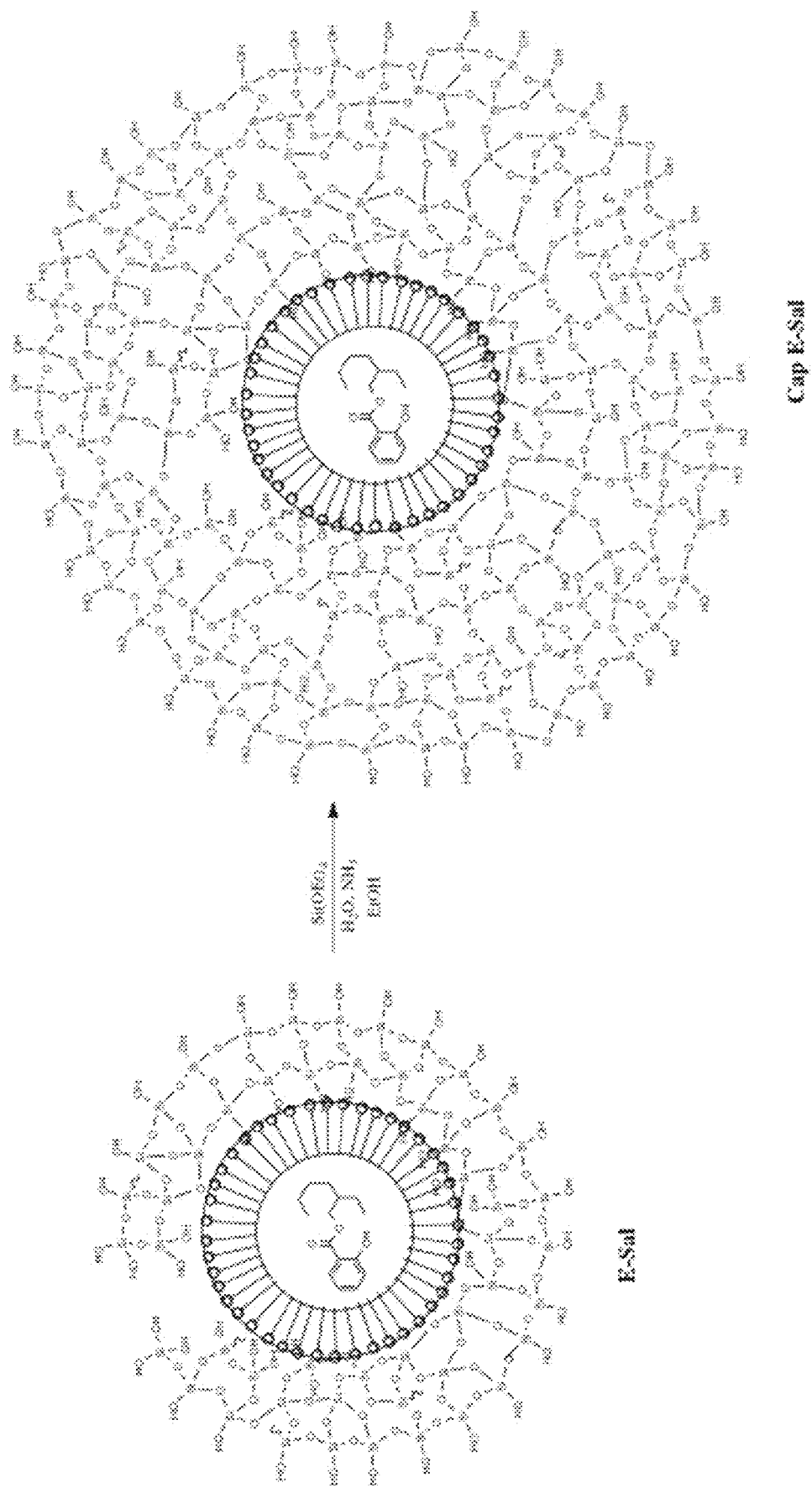
FIG. 13 shows a scheme of capping of physically encapsulated sunscreens by adding a second layer or cap of silica over the first.

Some of the hollow salicylate particles were reinforced with an additional layer of silica (Cap-E-Sal) as an alternative approach to reducing sunscreen leakage, as depicted in FIG. 13, which has been successfully applied to reducing fluorescent dye and drug leakage, but has not been reported for sunscreens.

Materials

All reagents were used as received without further purification unless otherwise stated. Sunscreen monomers were stored by freezing in benzene solutions.

Salicylate monomers: Salicylic acid (99%), 2-hydroxyterephthalic acid (97%), 3-aminopropyltriethoxysilane (APTES, 99%), N,N-dimethylformamide (DMF, anhydrous), triethylamine (Et$_3$N, 99.5%), and benzene (99.8%), were purchased from Sigma-Aldrich Corporation (St. Louis, Mo., USA). Thionyl chloride (SOCl$_2$, 98%) was purchased from Pfaltz & Bauer (Waterbury, Conn., USA). 3-Aminopropyltriethoxysilane was distilled from calcium hydride before use.

Curcuminoid Monomer: Curcumin (70%) was purchased from Sigma-Aldrich Corporation (St. Louis, Mo., USA), and potassium carbonate (K$_2$CO$_3$, anhydrous, 99%) was purchased from EMD Chemicals, Inc. (San Diego, Calif., USA). 3-Isocyanatopropyltriethoxysilane (IPTES, 95%) was purchased from Gelest, Inc. (Morrisville, Pa., USA) and distilled from calcium hydride before use.

Silica Particles: Tetraethoxysilane (TEOS, 98%), EtOH (anhydrous 99.5%), and cetyltrimethylammonium bromide (CTAB, ≥99%), were purchased from Sigma-Aldrich Corporation (St. Louis, Mo., USA). Ammonium hydroxide (NH$_4$OH, 28-30%) was purchased from EMD Chemicals, Inc. (San Diego, Calif., USA). 2-Ethylhexyl salicylate (>98%) was purchased from TCI America (Portland, Oreg., USA). TEOS was distilled from calcium hydride before use, and ethanol was refluxed over and distilled from magnesium turnings before use. NH$_4$OH (14.845 M) was titrated with hydrochloric acid (HCl), which was previously standardized with sodium carbonate (Na$_2$CO$_3$).

Materials Characterization

Column chromatography was performed on silica gel (60 Å, 70-230 mesh, 63-200 µm) purchased from Sigma-Aldrich Corporation (St. Louis, Mo., USA). For silsesquioxane monomers, silica gel was treated before using with a 1:150 TEOS:hexanes solution (v/v) followed with hexanes to remove residual TEOS. Then column was flushed with the eluent stated in the detailed experimental procedures below. Reaction progress was monitored by thin layer chromatography on Baker-Flex® Precoated Flexible Sheets (IB-F). Melting points were measured on a SRS EZ-Melt Automated Melting Point Apparatus and are uncorrected.

Infrared Spectroscopy (IR) was performed on a Thermo Scientific Nicolet™ iS™5 FT-IR Spectrometer. Solid samples were prepared by grinding with KBr into a pellet, while liquid samples were sandwiched between two NaCl plates. $^1$H and $^{13}$C Nuclear Magnetic Resonance Spectroscopy ($^1$H NMR and $^{13}$C NMR, respectively) were performed on a Bruker Avance-III 400 MHz Spectrometer at 298 K. Chemical shifts are reported in parts per million (ppm), by reference to the hydrogen residues of deuterated solvents as internal standard. CDCl$_3$: δ=7.26 ppm OH NMR) and δ=77.16 ppm ($^{13}$C NMR) Signals are described as s (singlet), d (doublet), t (triplet), q (quartet), p (pentet), sex. (sextet), sep. (septet), dd (doublet of doublets), dt (doublet of triplets), and m (multiplet). All coupling constants (J) are in hertz (Hz). High resolution and low resolution mass spectrometry (MS) were performed on a Bruker 9.4 T Apex-Qh hybrid Fourier transfer ion-cyclotron resonance (FT-ICR) instrument equipped with a dual ESI/MALDI source UV-Vis absorbance spectroscopy was obtained on a Shimadzu UV-Probe PC2501 UV-Vis Double Beam Spectrophotometer. Fluorescence was measured at 445 nm for the salicylates and 500 nm for curcuminoid on a PTI Quanta Master 40 Steady State Spectrofluorimeter. Excitation wavelengths of 324 nm (salicylate) and 420 nm (curcuminoid) were used. Dynamic Light Scattering (DLS) of ethanolic suspensions of particles (3 mg/mL) was performed using a Malvern Zetasizer Nano ZS90 at 20° C. and 173° C.

Scanning Electron Microscopy (SEM) was performed on gold-sputter coated samples with an FEI Inspec-S electron microscope with an accelerating voltage of 30 keV. Ethanol suspensions of particles (3 mg/mL) were dropcast onto a clean silicon wafer and evaporated to dryness before gold coating and analysis. Transmission Electron Microscopy (TEM) of particle samples dispersed on a grid were analyzed with a Hitachi H8100 electron microscope with an accelerating voltage of 200 kV and a high brightness LaB6 electron source.

Nitrogen adsorption-desorption isotherms of dry particles were measured with Nitrogen Adsorption Porosimetry on a Quantachome Autosorb-1 Porosimeter at 77.35 K. Particle samples were degassed at 100° C. for 24 h under vacuum. Specific surface areas were determined by the Multipoint Brunauer-Emmett-Teller (BET) method, as known to one of ordinary skill in the art. Pore size distributions were determined by the Barrett-Joyner-Halenda (BJH) model to the desorption isotherm, as known to one of ordinary skill in the art.

Monomer Synthesis

2-Hydroxybenzoyl chloride (1) (Scheme 1): A flame-dried, single-neck round-bottom flask fitted with a reflux condenser and magnetic stir bar was charged with salicylic acid (3.41 g, 22.73 mmol), SOCl$_2$ (8.62 mL) and DMF (8 drops) under argon and the reaction mixture was stirred at reflux (90° C.) for 48 h. The acid dissolved to a clear pale yellow solution upon addition of DMF. After cooling to room temperature, SOCl$_2$ was removed by alternately adding toluene and removing volatiles in vacuo 4× to afford a slightly translucent pale yellow oil (3.54 g, 99%), which was used in the synthesis of 2 without further purification.

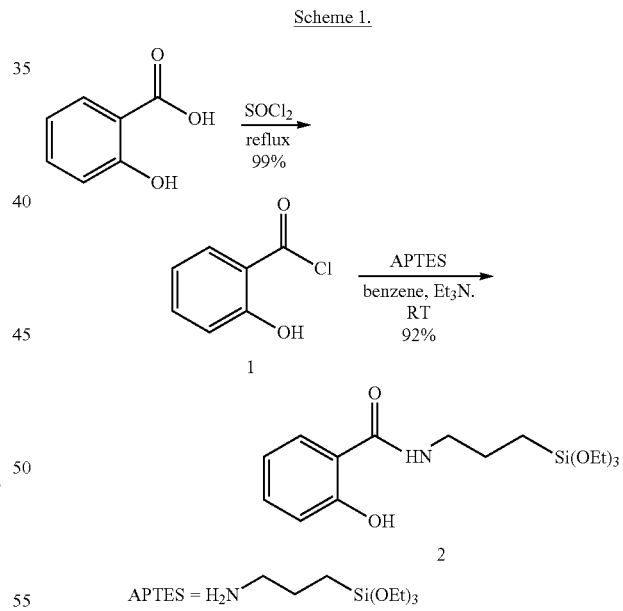

Scheme 1.

Protocol for synthesis of pendant (2) salicylate precursor.
Condensation of salicylic acid with APTES via salicyloyl chloride (1).

2-Hydroxy-N-(3-(triethoxysilyl)propyl)benzamide (2) (Scheme 1): A single-neck round-bottom flask fitted with a magnetic stir bar was charged with APTES (5.33 mL, 22.6 mmol) and Et$_3$N (3.64 mL, 26.14 mmol) in benzene (25 mL). To this, a separate solution of 1 (3.54 g, 22.63 mmol) in benzene (20 mL) was added dropwise at 0° C. to minimize the evolution of a white fog, using excess benzene (5 mL) to facilitate transfer. The reaction mixture was then stirred at 24° C. until consumption of starting material (48 h), monitoring by TLC (5:1 dichloromethane:ethyl acetate). Solid white triethylammonium chloride was removed via vacuum filtration, and volatiles removed in vacuo. The clear, pale yellow oil was purified by running through a silica plug (5:1 dichloromethane:ethyl acetate) and concentrating in vacuo to afford a clear, colorless oil (7.10 g, 92%). $^1$H NMR (400 MHz, CDCl$_3$, 25° C.): δ 0.70 (m, 2H, NHCH$_2$CH$_2$CH$_2$Si), 1.22 (t, J=7.0 Hz, 9H, OCH$_2$CH$_3$), 1.76 (m, 2H, NHCH$_2$CH$_2$CH$_2$Si), 3.44 (m, 2H, NHCH$_2$CH$_2$CH$_2$Si), 3.82 (q, J=7.0 Hz, 6H, OCH$_2$CH$_3$), 6.80 (ddd, 1H, J=8.0, 7.0, 1.2 Hz, C(5)H), 6.92 (br s, 1H, NH), 6.94 (ddd, J=8.4, 1.2, 0.4 Hz, 1H, C(3)H), 7.35 (ddd, J=8.4, 7.1, 1.6 Hz, 1H, C(4)H), 7.39 (dd, J=8, 1.6, 1H, C(6)H), 12.48 (s, 1H, ArOH); $^{13}$C NMR (101 MHz, CDCl$_3$, 25° C.): δ 7.88 (NHCH$_2$CH$_2$CH$_2$Si), 18.35 (OCH$_2$CH$_3$), 22.72 (NHCH$_2$CH$_2$CH$_2$Si), 41.75 (NHCH$_2$CH$_2$CH$_2$Si), 58.65, (OCH$_2$CH$_3$), 114.60, (C(1)-CO), 118.53, (C(3)-H), 118.55 (C(5)-H), 125.56 (C(6)-H), 134.03 (C(4)-H), 161.62, (C(2)-OH), 170.08 (C=O). IR (ν$_{max}$, cm$^{-1}$): 3382, 3019, 2976, 2928, 2400, 1641, 1596, 1539, 1490, 1447, 1363, 1304, 1215, 1169, 1075, 929, 758, 668. HR-MS (ESI, [M$^+$]) m/z: Calcd for C$_{16}$H$_{27}$NO$_5$Si: 341.1658 Found: 341.1569.

2-Hydroxyterephthaloyl dichloride (3) (Scheme 2): A flame-dried single-neck round-bottom flask fitted with a reflux condenser and magnetic stir bar was charged with 2-hydroxyterephthalic acid (0.706 g, 3.76 mmol), SOCl$_2$ (8.62 mL) and DMF (8 drops) under argon and the reaction mixture was stirred at reflux (90° C.) for 48 h. The acid dissolved to a clear yellow solution upon addition of DMF. After cooling to room temperature, SOCl$_2$ was removed by repeatedly adding toluene and removing volatiles in vacuo (4×) to afford a yellow solid (0.823 g, 97%), which was used in the synthesis of 4 without further purification.

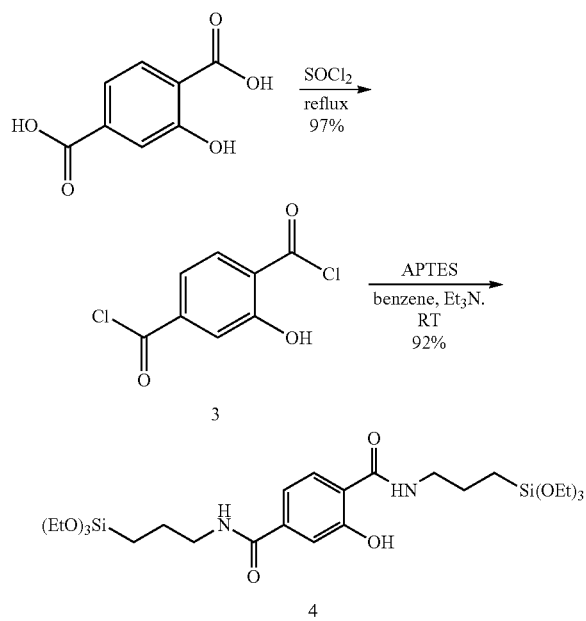

Scheme 2.

Protocol for synthesis of bridged (4) salicylate precursor.
Condensation of condensation of 2-hydroxyterephthalic acid with two equivalents of (3-aminopropyl)triethoxysilane (APTES) via 2-hydroxyterephthaloyl chloride (3).

2-Hydroxy-N',N''-bis(3-triethoxysilylpropyl)terephthalamide (4) (Scheme 2): A single-neck round-bottom flask fitted with a magnetic stir bar was charged with (APTES (1.8 mL, 7.52 mmol) and Et$_3$N (1.11 mL, 7.896 mmol) in benzene (25 mL). To this, a separate solution of 3 (0.823 g, 3.76 mmol) in benzene (20 mL) was added dropwise at 0° C. to minimize the evolution of a white fog, using excess benzene (5 mL) to facilitate transfer. The reaction mixture was stirred at 24° C. until consumption of starting material (48 h), monitoring by thin layer chromatography (TLC) on silica plates (2:1 ethyl acetate:dichloromethane). White triethylammonium chloride was filtered off and solvent was removed in vacuo. The clear, dark yellow oil was purified by running through a silica plug (2:1 ethyl acetate:dichloromethane) and concentrating in vacuo to afford a clear, dark yellow, tacky solid (2.13 g, 96%). $^1$H NMR (400 MHz, CDCl$_3$) δ 0.62 (m, 4H, NHCH$_2$CH$_2$CH$_2$Si), 1.134 (t, J=7.0 Hz, 9H, OCH$_2$CH$_3$), 1.142 (t, J=7.0 Hz, 9H, OCH$_2$CH$_3$), 1.68 (m, 4H, NHCH$_2$CH$_2$CH$_2$Si), 3.37 (m, 4H, NHCH$_2$CH$_2$CH$_2$Si), 3.74 (q, J=7.0 Hz, 6H, OCH$_2$CH$_3$), 3.75 (q, J=7.0 Hz, 6H, OCH$_2$CH$_3$) 6.55 (t, J=5.6 Hz, 1H, NH), 7.06 (t, J=5.6 Hz, 1H, NH), 7.15-7.17 (m, 2H, C(3)H and C(5)H), 7.39 (d, J=8.2 Hz, 1H, C(6)H), 12.44 (s, 1H, ArOH): $^{13}$C NMR (101 MHz, CDCl$_3$) δ 7.98 (NHCH$_2$CH$_2$CH$_2$Si), 18.39 (OCH$_2$CH$_3$), 22.65 (NHCH$_2$CH$_2$CH$_2$Si), 22.86 (NHCH$_2$CH$_2$CH$_2$Si), 41.87 (NHCH$_2$CH$_2$CH$_2$Si), 42.40 (NHCH$_2$CH$_2$CH$_2$Si), 58.65 (OCH$_2$CH$_3$), 58.72 (OCH$_2$CH$_3$), 114.26 (C(1)C=O), 116.22 (C(3)H), 117.28 (C(5)H), 125.88 (C(6)H), 139.94 (C(4)C=O), 161.52 (C(2)OH), 166.39 (C(7)=O), 169.29 (C(8)=O). IR (ν$_{max}$, cm$^{-1}$): 3683, 3619, 3019, 2976, 2400, 1647, 1528, 1423, 1215, 1075, 929, 759, 669. HR-MS (ESI, [M+H$^+$]) m/z: Calcd for C$_{25}$H$_{49}$N$_2$O$_9$Si$_2$: 589.2977 Found: 589.2991.

2-Methoxy-4-((1E,6E)-7-(3-methoxy-4-(((3-(triethoxysilyl)propyl)carbamoyl) oxy)phenyl)-3-oxo-5-(3-(triethoxysilyl)propoxy)hepta-1,6-dien-1-yl)phenyl(3-(triethoxysilyl)propyl)carbamate (6) (Scheme 3): A single-neck round-bottom flask fitted with a magnetic stir bar was charged with curcumin (1.0 g, 1.90 mmol) in anhydrous tetrahydrofuran (25 mL). To this, K$_2$CO$_3$ (0.663 g, 4.75 mmol) was added and the orange solution immediately turned a dark red. The reaction mixture was allowed to stir 24 h at 24° C. Afterwards, freshly distilled 3-isocyanatopropyltriethoxysilane (IPTES) (0.941 mL, 3.80 mmol) was added. The mixture was stirred at 24° C., monitoring by TLC (2:1 ethyl acetate: dichloromethane) until consumption of starting material (48 h). The red solution containing suspended solids was vacuum filtered, concentrated, and purified through silica plug (2:1 ethyl acetate:dichloromethane) to afford a clear red oil which solidified to a translucent tacky solid upon standing (1.174 g, 56%). $^1$H NMR (400 MHz, CDCl$_3$) δ 0.68 (m, 6H, 3×NHCH$_2$CH$_2$CH$_2$Si), 1.22 (dt, J=7.0, 4.4 Hz, 27H, OCH$_2$CH$_3$), 1.65-1.77 (m, 6H, 3×NHCH$_2$CH$_2$CH$_2$Si), 3.27 (m, 6H, 3×NHCH$_2$CH$_2$CH$_2$Si), 3.74-3.86 (m, 24H, 3×OCH$_2$CH$_3$ and 1 OCH$_3$), 5.41 (t, 1.7H, NH), 5.47 (t, 0.3H, NH), 5.82 (s, 1H, C(4)-H), 6.52 (d, J=15.8 Hz, 2H, (C(2,6)H), 7.10 (m, 6H, C(9,9',12,12',13,13')H), 7.56-7.66 (m & d, J=15.7 Hz, 2H); $^{13}$C NMR (101 MHz, CD$_2$Cl$_2$) δ 7.56, 7.65, 7.76 (NHCH$_2$CH$_2$CH$_2$Si), 18.32 (OCH$_2$CH$_3$), 23.09, 23.16, 25.12 (NHCH$_2$CH$_2$CH$_2$Si), 43.59, 43.72, 45.39 (NHCH$_2$CH$_2$CH$_2$Si), 55.97 (OCH$_3$), 58.47, 58.50, 58.53 (OCH$_2$CH$_3$), 101.69 (C(4)-H), 111.47 (C(13,13')H), 121.10 (C(9,9')H), 122.01 (C(5)-O), 123.68 (C(12,12')H), 123.99 (C(2,6)H), 129.12 (small amount of isomer), 133.36 (C(8,8')H), 140.10 (C(1,7)H), 141.7 (C(10, 10')OCH$_3$), 151.99 (2 C(11,11')-OC=O), 153.98 (3 NHC=O), 183.14 (C=O). IR (ν$_{max}$, cm$^{-1}$): 3346, 3053, 2975, 2928, 1740, 1628, 1587, 1510, 1464, 1390, 1265, 1206, 1165, 1124, 1077, 1034, 961, 909, 848, 739, 704, 667. HR-MS (ESI, [M+Na$^+$]) m/z: Calcd for $C_{51}H_{83}N_3NaO_{18}Si_3$: 1132.4877; Found: 1132.4878.

Scheme 3: Synthesis of bridged circuminoid (6)

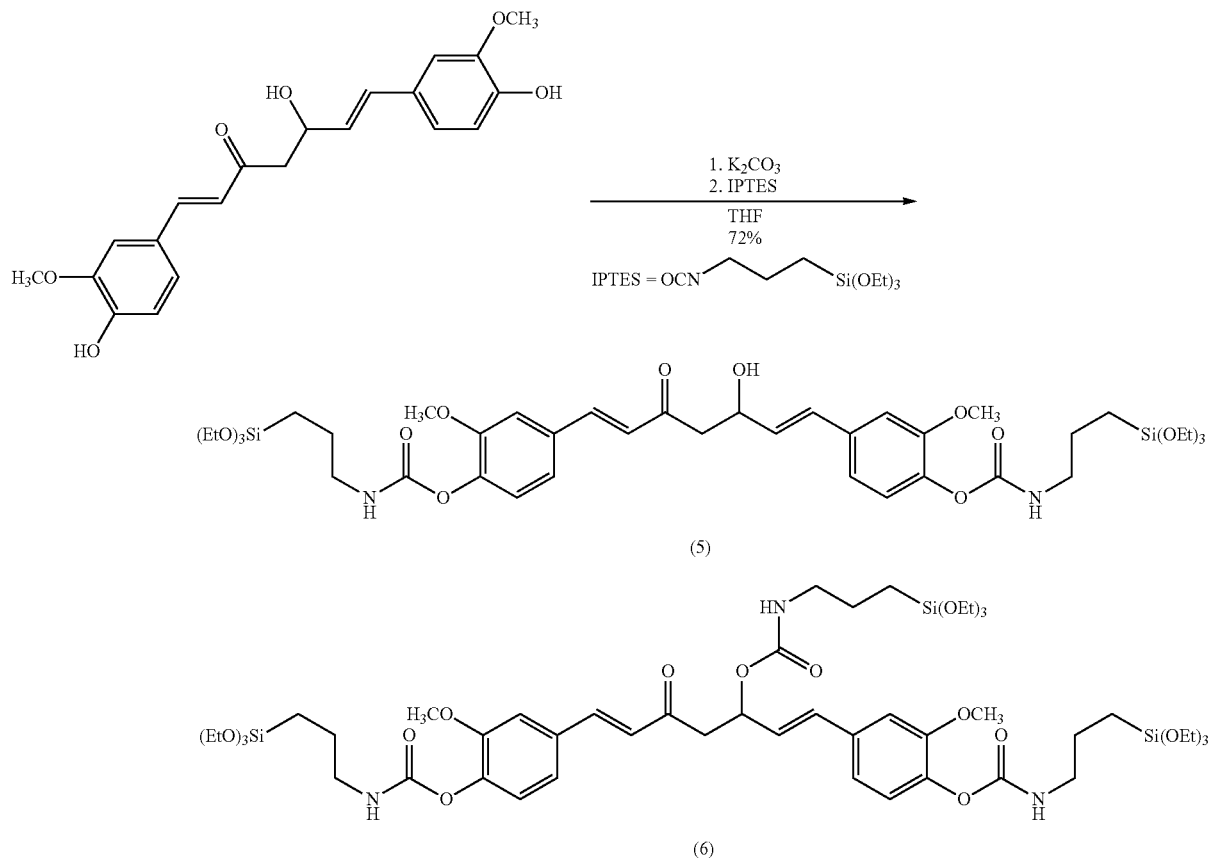

Particle Preparation Procedures

Unmodified surfactant template silica particles: A 250 mL single-neck round-bottom flask fitted with a magnetic stir bar was charged with CTAB (0.32 g, 0.89 mmol) in anhydrous ethanol (60 mL) and distilled water (102 mL). To this, TEOS (2.0 mL, 8.96 mmol) was added and the clear solution stirred 5 min at 24° C. Finally, aq. NH$_4$OH (13.4 M, 2.0 mL) was added and the solution stirred 3 h at 24° C. (700 RPM). Sphere evolution was indicated by an increasing opalescence of the mixture beginning 2 min after adding the NH$_4$OH solution. The transition to a turbid white suspension occurred within a few more minutes. After 3 h, the product was centrifuged to remove excess catalyst and starting material, and then washed 3× with water (0.581 g). Hydrodynamic diameter (DLS)=800±126 nm. Diameter (SEM) =760±57 nm. BET surface area=6 m$^2$/g. BJH pore size=31 Å.

Physically encapsulated salicylate particles (E-Sal): A 250 mL single-neck round-bottom flask fitted with a magnetic stir bar was charged with CTAB (0.32 g, 0.89 mmol) in anhydrous ethanol (40 mL) and distilled water (102 mL). To this, a previously prepared solution of 2-ethylhexyl salicylate (0.023 g, 0.089 mmol) in anhydrous ethanol (20 mL) was added. Afterwards, TEOS (2.0 mL, 8.96 mmol) was added and the clear solution stirred 5 min at 24° C. Finally, aq. NH$_4$OH (13.4 M, 2.0 mL) was added and the solution was stirred 3 h at 24° C. (700 RPM). Sphere evolution was indicated by an increasing opalescence of the mixture beginning 2 min after adding the NH$_4$OH solution. The transition to a turbid white suspension occurred within a few more minutes. After 3 h, the product was centrifuged to remove excess catalyst and starting material, then washed 3× with water (0.724 g, yield=135% based on silica only). Hydrodynamic diameter (DLS)=830±56 nm. Diameter (SEM) =657±71 nm. BET surface area=9 m$^2$/g. BJH pore size=31 Å.

Capped physically encapsulated salicylate particles (cap E-Sal): A 50 mL single-neck round-bottom flask equipped with a magnetic stir bar was charged with a suspension of E-Sal (0.272 g) in anhydrous ethanol (20 mL). To this, NH$_4$OH (13.4 M, 1.6 mL) and then freshly distilled TEOS (0.30 mL, 1.34 mmol) were added, and the suspension was allowed to stir at 24° C. for 24 h. Afterwards, the product was centrifuged to remove excess catalyst and starting material, then washed 3× with ethanol (0.292 g, 83% based on full conversion and addition of silica from TEOS). Hydrodynamic diameter (DLS)=868±119 nm. Diameter (SEM)=809±80 nm. BET surface area=6 m$^2$/g. BJH pore size=16 Å.

Un-modified Stöber silica particles: A 100 mL, 3-neck, round-bottom flask was equipped with a thermometer and magnetic stir bar. The flask was charged with anhydrous ethanol (33.1 mL) and aq. NH$_4$OH (5.154 M, 20.1 mL) and the solution stirred at 30° C. In a scintillation vial in the same water bath, TEOS (5 mL) was heated to 30° C. Once the temperatures of both solutions had equilibrated at 30° C., TEOS was added to the reaction flask and the resultant solution was allowed to stir 15 s. Afterwards, stirring was stopped and the reaction mixture was allowed to stand at 30° C. for 2 h. Sphere evolution was indicated by an increasing opalescence of the mixture beginning 1-5 minutes after adding TEOS. The transition to a turbid white suspension occurred within a few more minutes. After 2 h, the product was centrifuged to remove excess catalyst and starting material, then washed 3× with ethanol (1.569 g, yield=117% based on fully condensed structure). Hydrodynamic diameter (DLS)=556±34 nm. Diameter (SEM)=520±58 nm. BET surface area=12 m$^2$/g. BJH pore size=3 Å.

Pendant salicylate particles (P-Sal): A 100 mL, 3-neck, round-bottom flask was equipped with a thermometer and magnetic stir bar. The flask was charged with anhydrous ethanol (33.1 mL) and aq. NH$_4$OH (5.154 M, 20.1 mL) and the solution stirred at 30° C. In a scintillation vial in the same water bath, a previously prepared 1 mole % monomer solution of 2 in TEOS (5 mL) was heated to 30° C. Once the temperatures of both solutions had equilibrated at 30° C., monomer solution was added to the reaction flask and the resultant solution was allowed to stir 15 s. Afterwards, stirring was stopped and the reaction mixture was allowed to stand at 30° C. for 2 h. Sphere evolution was indicated by an increasing opalescence of the mixture beginning 1-5 min after adding the monomer solution. The transition to a turbid white suspension occurred within a few more minutes. After 2 h, the product was centrifuged to remove excess catalyst and starting material, then washed 3× with ethanol (1.539 g, yield=114% based on fully condensed structure). Hydrodynamic diameter (DLS)=781±42 nm. Diameter (SEM) =657±71 nm. BET surface area=13 m$^2$/g. BJH pore size=31 Å.

Bridged salicylate particles (B-Sal): A 100 mL, 3-neck, round-bottom flask was equipped with a thermometer, reflux condenser, and magnetic stir bar. The flask was charged with anhydrous ethanol (33.1 mL) and aq. NH$_4$OH (5.154 M, 20.1 mL) and the solution stirred at 30° C. In a scintillation vial in the same water bath, a previously prepared 1 mole % monomer solution of 4 (0.131 g, 0.224 mmol) in TEOS (5 mL) was heated to 30° C. Once the temperatures of both solutions had equilibrated at 30° C., monomer solution was added to the reaction flask and the resultant solution was allowed to stir 15 s. Afterwards, stirring was stopped and the reaction mixture was allowed to stand at 30° C. for 2 h. Sphere evolution was indicated by an increasing opalescence of the mixture beginning 1-5 min after adding the monomer solution. The transition to a turbid white suspension occurred within a few more minutes. After 2 h, the product was centrifuged to remove excess catalyst and starting material, then washed 3× with ethanol (1.608 g, yield=120% based on fully condensed structure). Hydrodynamic diameter (DLS)=795±33 nm. Diameter (SEM) =668±74 nm. BET surface area=7 m$^2$/g. BJH pore size=19.5 Å.

Bridged curcuminoid particles (B-Curc); A 100 mL, round-bottom flask was equipped with a thermometer and magnetic stir bar. The flask was charged with anhydrous ethanol (33.1 mL) and aq. NH$_4$OH (5.154 M, 20.1 mL) and the solution stirred at 30° C. In a scintillation vial in the same water bath, a previously prepared monomer solution of 6 (0.196 g, 0.175 mmol) in TEOS (5 mL, 4.70 g, 22.56 mmol) was heated to 30° C. Once the temperatures of both solutions had equilibrated at 30° C., monomer solution was added to the reaction flask and the resultant solution was allowed to stir 15 s. Afterwards, stirring was stopped and the reaction mixture was allowed to stand at 30° C. for 2 h. Sphere evolution was indicated by an increasing opalescence of the mixture beginning 1-5 minutes after adding the monomer solution. The transition to a turbid white suspension occurred within a few more minutes. After 2 h, the product was centrifuged to remove excess catalyst and starting material, and then washed 3× with ethanol. After drying, a creamy white powder was obtained (1.585 g, yield=118% based on fully condensed structure). Hydrodynamic diameter (DLS)=688±56 nm. Diameter (SEM)=665±70 nm. BET surface area=5 m$^2$/g. BJH pore size=22 Å.

Leaching Analysis

Sunscreen particle suspensions in anhydrous ethanol (3 mg/mL) were stirred 24 h at 24° C. To remove particles, each sample was filtered (6×) through a 0.20 μm nylon syringe filter obtained from Sigma-Aldrich Corporation (St. Louis, Mo., USA). Efficacy of removal of particles from suspensions was checked with DLS and SEM analyses of the filtered and un-filtered solutions. Leaching was assessed with fluorescence spectroscopy before and after filtration. Sunscreen concentrations were calculated from prepared fluorescence vs. concentration calibration plots. Excitation wavelengths of 324 nm (salicylate) and 420 nm (curcuminoid) were used.

UV Stability Analysis

UV stability analysis was performed according to COLIPA standards. Sunscreen particle suspensions were dispersed in 70/30 ethanol/glycerin (10 wt %). Ethylhexyl salicylate solutions (10 wt %) in 70/30 ethanol/glycerin were prepared as experimental controls. The suspensions/solutions (18.5 mg) were dropcast onto a dean quartz slide (2.55 cm×3.63 cm) to ensure coverage of 2.0 mg/cm$^2$. A second quartz slide of the same dimensions was placed above the sample to sandwich it. Each sample was then irradiated with a Solar Simulator (Xe arc lamp, UVB=0.039 W/cm$^2$, UVA=0.052 W/cm$^2$) for 6 h, monitoring by UV-Vis absorbance spectroscopy at specified time intervals. After 6 h, the irradiated free sunscreen samples were washed from the quartz slide and analyzed by NMR or GC-MS. The criteria stipulated and chosen for the stability experiments are listed in Table B.

TABLE B

| Criteria for UV stability analysis of sunscreens. | | |
|---|---|---|
| Criteria | COLIPA(55) | This analysis |
| Solvent | 70% volatile + 30% non-volatile (v/v) | 70/30 ethanol/glycerin |
| Sample | Liquid film on quartz slide or in quartz cuvette (2.0 mg/cm$^2$) | Liquid film sandwiched between 2 quartz slide (2.0 mg/cm$^2$) |
| Concentration | Up to 15 wt % | 10 wt % |
| Light Source | Xenonlamp | Xenon lamp |
| Irradiance | 1-4 MED/h | 1 MED/h |
| Dose | Up to 10 MED | 6 MED |

*1 MED = 140.3 J/cm$^2$ (40)

In Vitro SPF and UVAPF Determinations

Incremental UV absorbance data for both the salicylate and curcuminoid particles (obtained during UV stability analysis) was utilized for these experiments. In vitro SPF values were then determined using erythemal effect (EE) and solar intensity (I) constants. In vitro UVA protection efficacy (UVAPF), namely critical wavelength and pre- and post-irradiation UVA/UVB ratios, as well as Boots Star Ratings, were also determined from the UV stability spectral data.

Results and Discussion
Monomer Syntheses

Chemical structures of each sunscreen monomer were designed to ensure the absorbance and emission profiles were similar to 2-ethylhexyl salicylate and curcumin. Monomer 2 is the amide of salicyclic acid and 3-aminopropyltriethoxysilane (APTES) (Scheme 1). Bridged salicylate 4 is the bis-amide prepared from 2-hydroxyterephthalic acid and APTES (Scheme 2). The salicylate monomers are both o-hydroxybenzamides, which ensures intramolecular hydrogen bonding and retention of UV absorbance from 267-340 nm. Curcuminoid monomer 6, which is the tris-carbamate of curcumin and 3-isocyanatopropyltriethoxysilane (IPTES; Scheme 3), retains the electron donating functionalities in the meta and para positions.

Synthesis of Salicylate Sunscreens

Salicylate monomers 2 and 4 were successfully synthesized in high yields via condensation of APTES with salicyloyl chloride 1 and 2-hydroxyterephthaloyl chloride 3, respectively (Schemes 1 & 2). The acid chlorides were synthesized from salicyclic add and 2-hydroxyterephthalic acid in near quantitative yields using modified literature procedures. Pendant monomer 2 had been previously prepared by condensation of ethyl salicylate with APTES without experimental details. Bridged monomer 4 has not been previously reported.

Synthesis of Bridged Curcuminoid Sunscreen

Curcumin is composed of a mixture of isomers that contain an average of two methoxy and two phenol hydroxyl groups as seen in Scheme 3. Commercial samples are typically purified to only 75-85%, meaning the position and extent of methoxylation of the phenol hydroxyl groups varies. As such, the proposed curcuminoid monomer includes all natural derivatives of the parent curcumin. Since the major constituents possess a bis-phenol residue, preparation of the bridged silsesquioxane analogue simply entailed (1) deprotonation with $K_2CO_3$ followed by (2) condensation with freshly distilled IPTES to afford not the bis-triethoxysilylcarbamate 5, but the tris-triethoxysilylcarbamate 6 (Scheme 3). Synthesis of an analogue of 5 is taught in US20070204412; and involves hydrosilylation of 4,4'-bisallyloxycurcumin with $HSi(OEt)_3$ (74% crude) to form monomers with ether linkages. The carbamate route of the present invention was a more direct and less costly approach to preparing a bridged curcumin, and good yields were obtained (72%). In some embodiments, higher yields can be obtained by anticipating three equivalents of the isocyanatopropyltriethoxysilane reacting with each curcumin. Without wishing to limit the invention a particular theory or mechanism, the tris-triethoxysilylcarbamate monomer 6 is better suited as a sunscreen than 5, as the monomer is locked into the enol configuration with its extended conjugation and strong absorption, whereas 5 would be a mixture of the enol and diketone isomers.

Spherical Particle Preparation

All sunscreen particle samples were prepared in triplicate with 1 mole % of the sunscreen with respect to TEOS. Unmodified silica particles were also prepared to examine the effect of sunscreen incorporation on resultant particle size. Particles are described in terms of their diameter determined by SEM rather than their hydrodynamic diameter determined by dynamic light scattering. Particle yields greater than 100% are common in sol-gel polymerization reactions and were expected, as the final product generally contains un-reacted alkoxysilane and silanol groups.

Figure 3A:
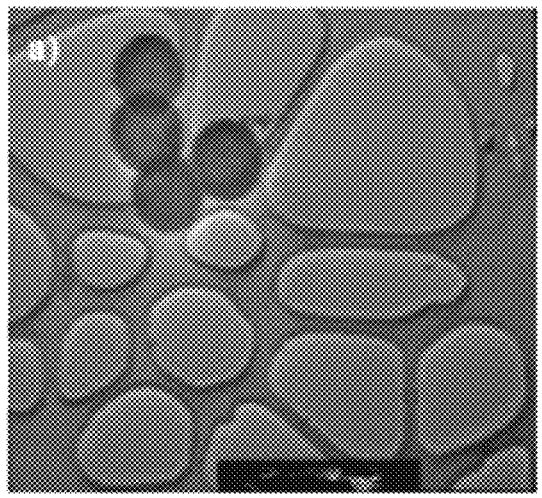
FIGS. 3A-3D shows TEM micrographs of E-Sal (FIG. 3A), cap E-Sal particles (FIG. 3B), unmodified silica particles prepared via microemulsion polymerization (FIG. 3C), and unmodified silica particles prepared via sol-gel polymerization (FIG. 3D). The shell thicknesses in FIGS. 2A and 3B are approximately 150±20 nm and 203±29 nm, respectively, implying a cap thickness of 53 nm according to TEM.
Figure 3B:
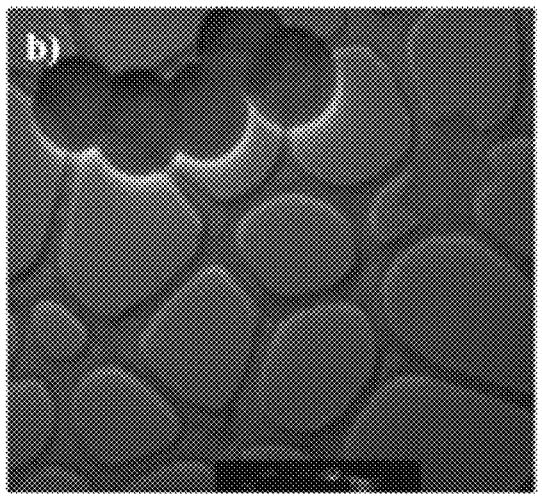
Figure 3C:
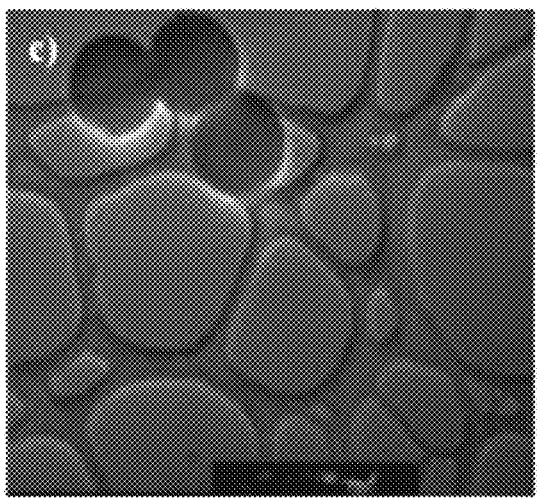
Figure 3D:
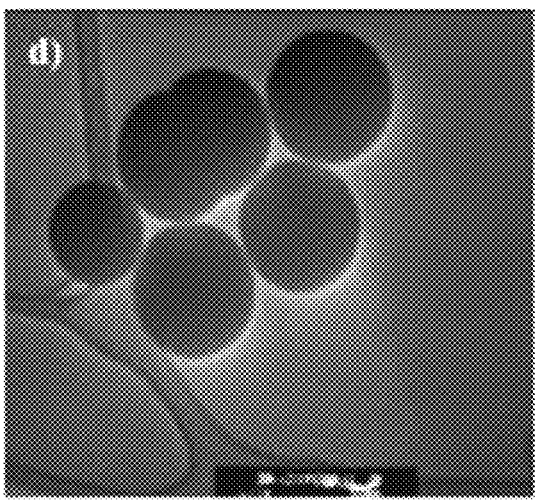

Physical Encapsulation of 2-Ethylhexyl Salicylate Via Microemulsion Polymerization Silica particles containing 2-ethylhexyl salicylate, physically encapsulated within the hollow core, (E-Sal) were successfully prepared via a modified O/W microemulsion technique. CTAB assembles into micelles containing TEOS and the hydrophobic sunscreen. Hydrolysis of the TEOS results in hydrophilic intermediates that react to form silica at the interface between the micelle and the water phase leaving the sunscreen to remain in the hollow interior of the particles. An ethanol/water ratio of 0.59 afforded salicylate filled particles with an average diameter of 743±78 nm (FIG. 2A), compared with hollow particles prepared without sunscreen exhibiting diameters of 761±57 nm (FIG. 2B). The SEM clearly reveals a ruptured particle (circled in red) highlighting the problem of release of sunscreen with mechanical damage to the silica shells. TEM micrographs demonstrate that the particles are hollow with a silica shell thickness of 150 nm (FIG. 3A).

Particle capping, i.e. fortifying of the particle surface with an additional silica layer, was performed on the E-Sal particles to determine if leaking of sunscreen from the hollow particles could be reduced. The average diameters of the capped particles (Cap E-Sal) increased to 809±81 nm by TEM (FIG. 3B), implying an average cap thickness of 50-60 nm. Comparison of the size of the particles in the SEM's for E-Sal and Cap E-Sal (FIGS. 2B and 2C) confirms the cap thickness.

Adsorption-desorption isotherms of E-Sal, Cap E-Sal, and hollow $SiO_2$ particles without sunscreen are reversible and convex over the entire pressure range, with an indistinct monolayer-multilayer $N_2$ adsorption point consistent with non-porous particles with weak adsorbent-adsorbate interactions (Type III isotherm). This is evidenced by the small pore volumes and BET surface areas, the latter of which are consistent with the calculated geometric surface areas, shown in Table 1.

TABLE 1

Nitrogen Porosimetry data for salicylate particles prepared via emulsion polymerization.

| Sample | Description | $S_{BET}$ (m²/g) | $S_{calc}$ (m²/g) | *$V_{BJH-d}$ (cm³/g) | #$d_{BJH}$ (Å) |
|---|---|---|---|---|---|
| E-Sal | Encapsulated salicylate in hollow silica particles | 8.6 | 3.0 | 0.11 | 30.7 |
| Cap E-Sal | Encapsulated and capped with more $SiO_2$ | 6.6 | 2.8 | 0.09 | 15.6 |
| $SiO_2$ no sunscreen | Stober silica particles | 6.5 | 3.0 | 0.08 | 30.7 |
| P-Sal | Salicylate attached via pendant silsesquioxane | 12.9 | 3.0 | 0.18 | 30.9 |
| B-Sal | Salicylate attached via bridged silsesquioxane | 6.9 | 3.4 | 0.15 | 19.5 |
| Unmodified $SiO_2$ | Stober silica particles | 12.1 | 4.4 | 0.22 | 34.3 |
| B-Curc | Curcuminoid attached via bridged silsesquioxane | 5.3 | 3.4 | 0.08 | 22.0 |

Figure 4A:
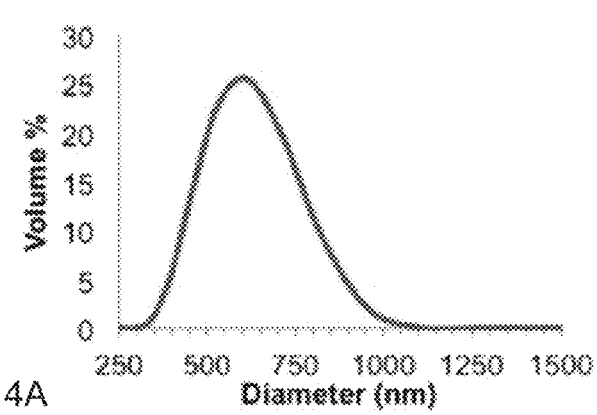
FIGS. 4A-4D show DLS spectra and SEM micrographs of unmodified silica particles (FIG. 4A), pendant salicylate particles (P-Sal) (FIG. 4B), bridged salicylate particles (B-Sal) (FIG. 4C), and bridged curcuminoid particles (B-Curc) (FIG. 4D). DLS data represents the average of three trials.
Figure 4A:
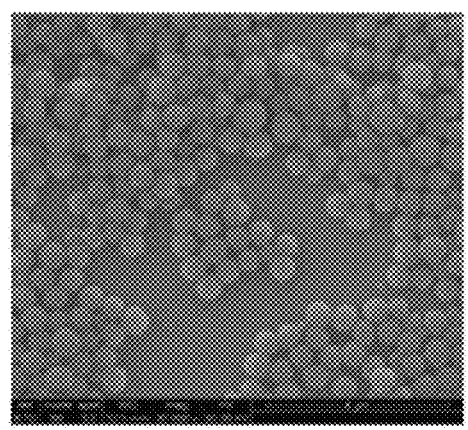
Figure 4B:
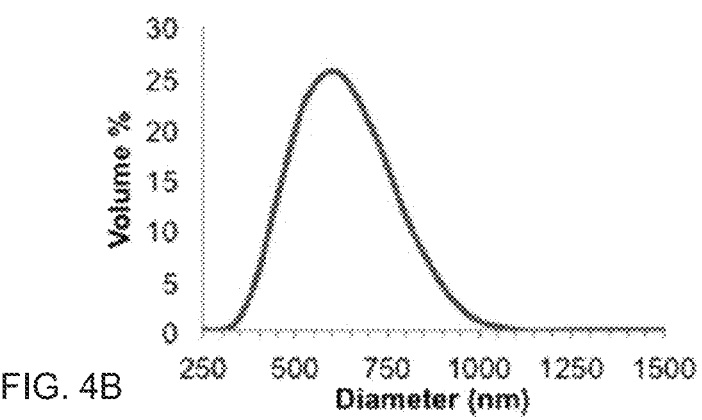
Figure 4B:
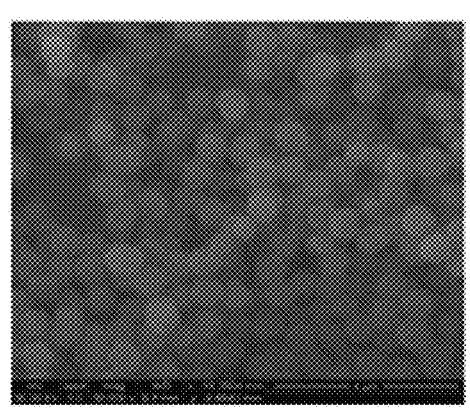
Figure 4C:
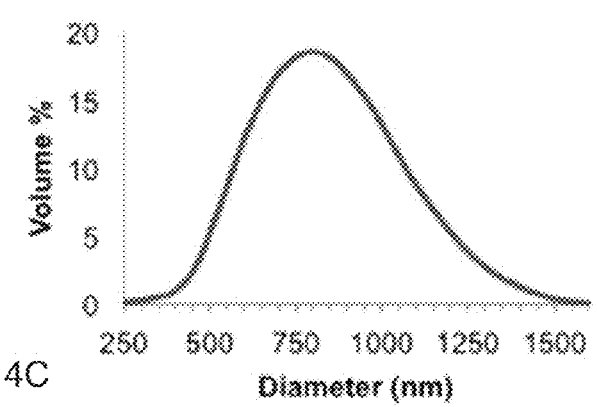
Figure 4C:
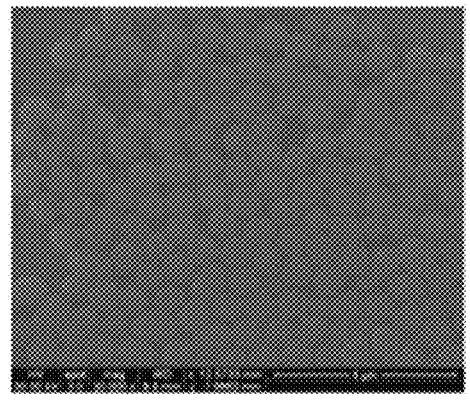

*BJH desorption cumulative pore vol. of pores in the range of 0-5000.0 Å;
Average pore diameter by BJH Covalently Incorporated Salicylate Particles Via Sol-Gel Polymerization Pendant salicylate (P-Sal) and bridged salicylate (B-Sal) particles were successfully prepared via co-condensation of sunscreen monomers 2 and 4 with TEOS. SEM and DLS analyses have confirmed that the P-Sal particles are spherical in shape and morphology with a mean diameter of 657±71 nm (FIG. 4B). The B-Sal particles, while mostly spherical, are more irregular in shape and slightly larger in diameter (668±74 nm) than the pendant samples (FIG. 4C). Additionally, some particles were fused together. Overall, salicylate incorporation resulted in larger particles compared to unmodified silica counterparts prepared only from TEOS (FIG. 4A).

Figure 5A:
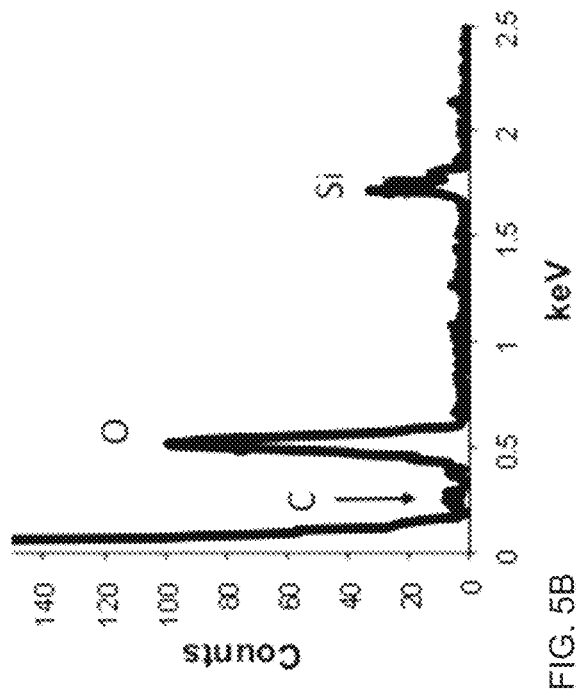
FIGS. 5A-5B show EDS spectra of P-Sal particles (FIG. 4A), and B-Sal particles (FIG. 4B). The P-Sal spectrum details the presence of silicon (Si), oxygen (O), and small amounts of carbon (C) atoms on the particle surface, while the B-Sal spectrum details the presence of only Si and O atoms on the surface.
Figure 5B:
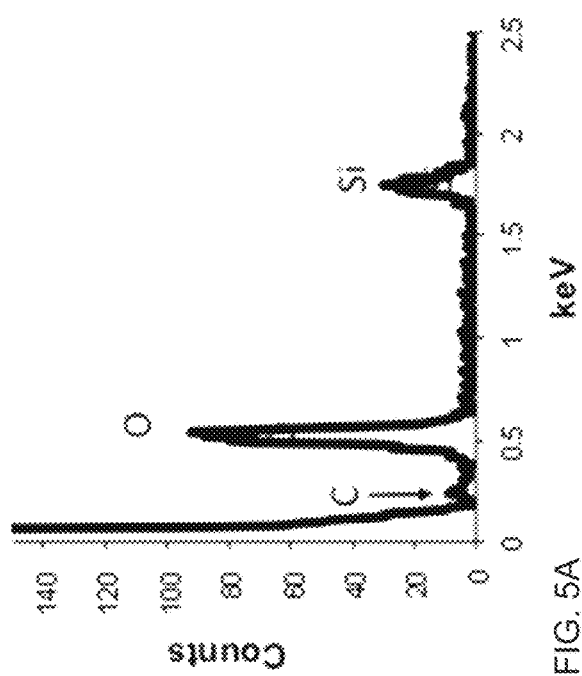

Monomers with single triethoxysilyl groups, such as 2, are reported to segregate to the surface of silica prepared by sol-gel co-polymerizations with TEOS. This is believed to arise from the steric bulk of the pendant organic group and the tendency to form cyclic siloxanes. Bridged monomers, such as 4 or 5, are generally believed to incorporate more uniformly through silica particles because the multiple silyl groups circumvent any steric hindrance to network formation. Energy Dispersive Spectroscopy (EDS), which allows for elemental surface analysis of substrates due to the shallow penetration depth of the electron probe, was used to examine the P-Sal and B-Sal particles (FIGS. 5A and 5B). In the P-Sal particles, silicon (Si), oxygen (O), and small amounts of carbon (C) atoms were seen on the surface. In the B-Sal particles only Si and O were observed. These results are consistent with more of the pendant monomer (2) segregating to the particles' surfaces than the bridged monomer (4). Like the particles prepared via microemulsion polymerization, the adsorption-desorption isotherms for P-Sal, B-Sal, and unmodified silica are of type Ill consistent with non-porous particles (Table 1).

Covalently Incorporated Curcuminoid Particles Via Sol-Gel Polymerization

Figure 4D:
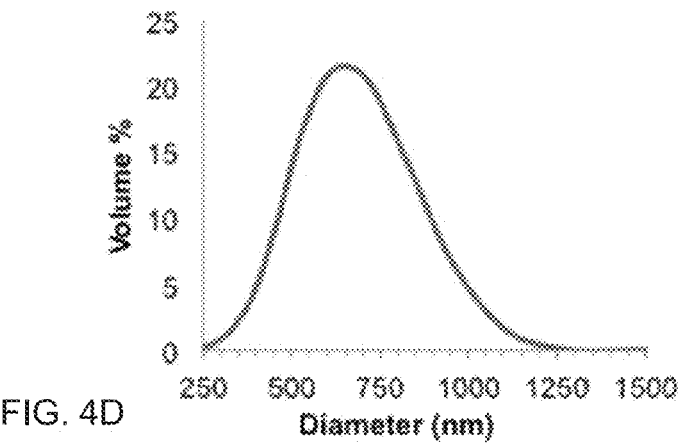
Figure 4D:
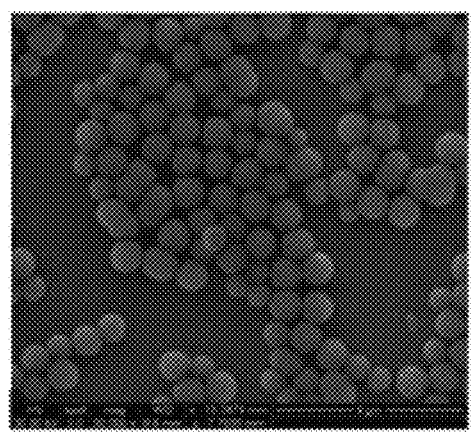

Bridged curcuminoid (B-Curc) particles are similar to the B-Sal particles with more irregular spherical shapes and fusing of particles together than with P-Sal particles (FIG. 4D). Average particle diameters of B-Curc are approximately the same as the B-Sal particles, at 665±70 nm, but larger than unmodified silica particles. The adsorption-desorption isotherm for B-Curc particles is of type III with small pore volumes and BET surface area, the latter of which is consistent with the calculated geometric surface areas (Table 1). As such, it can be deduced that the B-Curc particles are non-porous like the previously prepared salicylate and unmodified silica particle samples.

Quantification of Sunscreen Content in Particles

Fluorescence spectroscopy experiments were performed to quantify the sunscreen content (mg/g). Fluorescence was chosen due its greater sensitivity and less impact from scattering from the silica particles. Sunscreen loadings were calculated for each from the fluorescence spectra of 3.5 mL ethanolic particle suspensions (3.0 mg/mL) using standard calibration plots for 2-ethylhexyl salicylate and curcumin solutions. Compared to the theoretical 1.0 mole % sunscreen incorporation, the actual loading is approximately 5× less than theoretically calculated, as shown in Table 2. The fact that 80% of the sunscreen monomers failed to incorporate is likely due to the lower reactivity of the alkyl substituted triethoxysilyl groups under alkaline polymerization conditions compared with tetraethoxysilane. The remaining sunscreen monomers may have remained in solution or in suspension as smaller particles discarded during the centrifugation purification of the larger sunscreen particles.

TABLE 2

Sunscreen Loadings and percent leaching.

| Sample | Theoretical (mg/g) | Experimental (mg/g) | % Leached |
|---|---|---|---|
| E-Sal | 41.67 | 8.50 | 24.17 |
| Cap-E-Sal | 32.92 | 8.64 | 6.78 |
| P-Sal | 56.83 | 11.67 | 0.80 |
| B-Sal | 98.01 | 21.56 | 0.04 |
| B-Curc | 143.66 | 28.77 | 0.29 |

Given the Food and Drug Administration (FDA) recommended sunscreen application of 2.0 mg/cm$^2$, and the average surface area of human males (1.9 m$^2$) and females (1.71 m$^2$), approximately 34-38 g of sunscreen should be applied for full body protection. Using this mass, the maximum FDA allowable 2-ethylhexyl salicylate concentration of 5%, and the calculated values listed in Table 2, the sunscreen formulation would require the use of 235.3 g, 171.4 g, and 92.8 g of E-Sal, P-Sal, and B-Sal particles, respectively. A circuminoid formulation (using a maximum concentration of 3%) would require the use of 41.7 g of B-Curc particles. This is based on the particles prepared with 0.2 mol % covalently incorporated sunscreens.

Sunscreen Leaching Analysis

To maintain high levels of protection over time and minimize skin contact, the sunscreen must not leach from the silica particles. The first mode of analysis was to determine if covalent incorporation minimizes leaching over that of physical encapsulation. Without wishing to limit the invention to a particular theory or mechanism, it was hypothesized that minimal leaching would be achieved with covalent incorporation, as the silica shell of the physical samples are fragile and can easily rupture, and the sunscreen is only retained by electrostatic forces (FIG. 1A). If so, the second mode of analysis was to determine which mode of covalent incorporation (bridged or pendant) minimizes leaching. The increased number of bonding sites in the bridged sample (6) as opposed to the pendant analogue (3) would imply that more bonds are required to break before the ingredient can leach from the particle, thereby resulting in less leach out. Lastly, a third analysis was performed to determine if covalent incorporation would eliminate the need for an extra capping step. It was assumed that the magnitude of leaching from the covalent samples would be less than the capped physically encapsulated sample, thereby negating the need for capping.

Figure 6A:
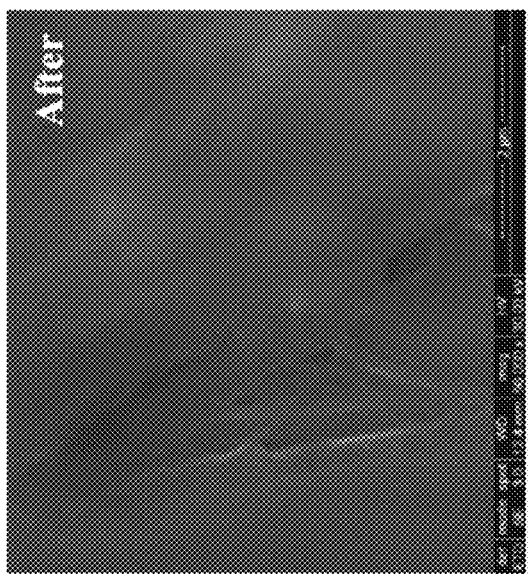
FIGS. 6A-6B show SEM micrographs of P-Sal particle suspensions used in leaching analysis before (FIG. 6A) and after (FIG. 6B) filtration, detailing successful removal of particles. Micrographs are representative of all particle samples analyzed (data not shown).
Figure 6B:
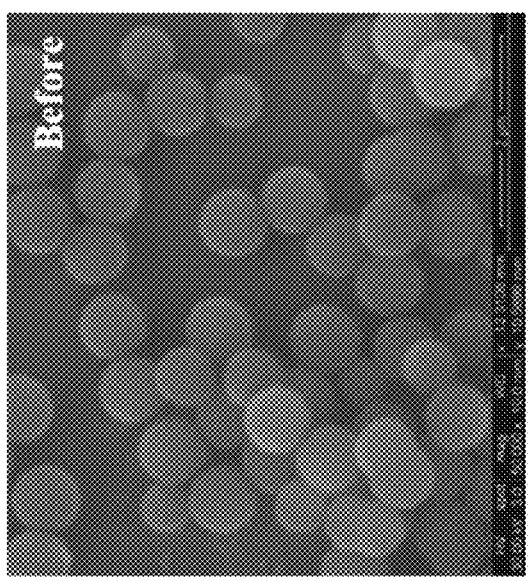

To test the above hypotheses, ethanolic salicylate particle suspensions (3.0 mg/mL) were stirred for 24 h at ambient temperature (24° C.), then filtered 6× times with a 0.2 µm microfilter to ensure fluorescence emission intensities were not the result of residual incorporated sunscreen. SEM results detailed the successful removal of particles from the ethanolic suspensions (FIGS. 6A and 6B).

Fluorescence spectra comparisons of the filtered and un-filtered particle suspensions (FIG. 7A-7E and Table 2) detail significant leaching (24.17%) when 2-ethylhexylsalicylate is physically encapsulated within silica particles. Since all prepared particle samples were determined to be non-porous, this failure of dye retention can be explained due to shell fragility and rupture of the particles (FIG. 2A), which can easily allow for leaching of 2-ethylhexyl salicylate from the particle core. While capping did reduce leach out to 6.78%, the capped samples were still outperformed by the covalent analogues.

Figures 7A, 7B, 7C, 7D, 7E:
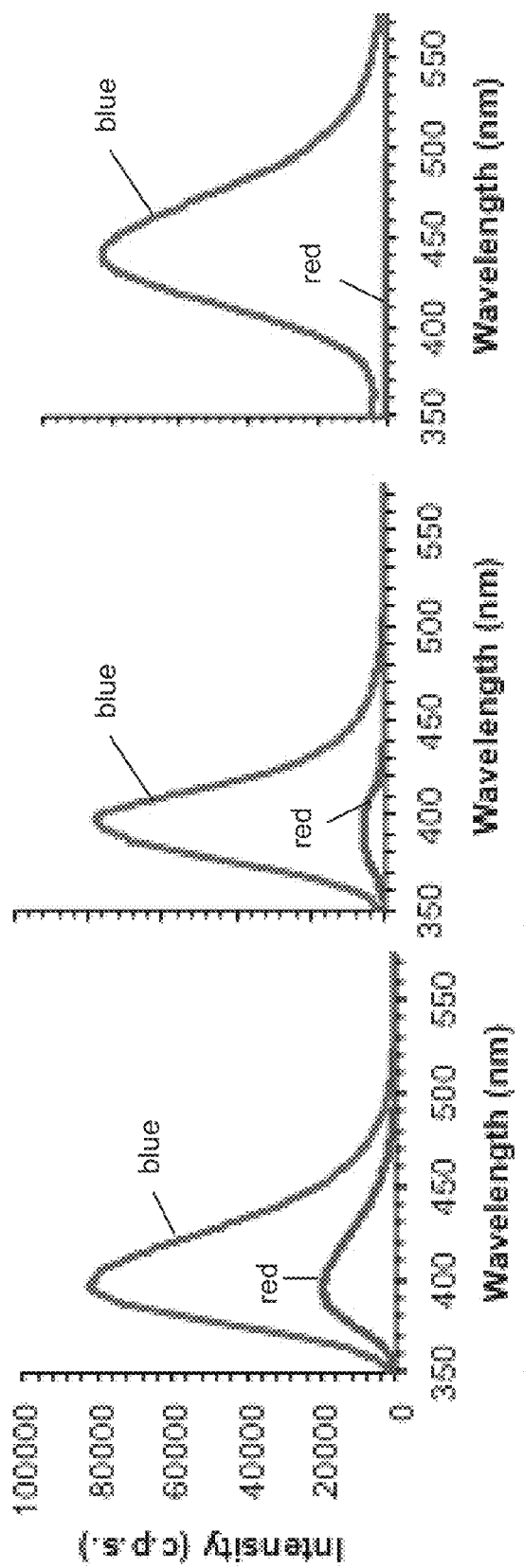
FIGS. 7A-7E show fluorescence spectra of E-Sal (FIG. 7A), Cap E-Sal (FIG. 7B), P-Sal (FIG. 7C), B-Sal (FIG. 7D), and B-Curc (FIG. 7E) particle samples before (blue) and after filtration (red). Overall, bridged incorporation was seen to minimize leaching the most.
Figure 8A:
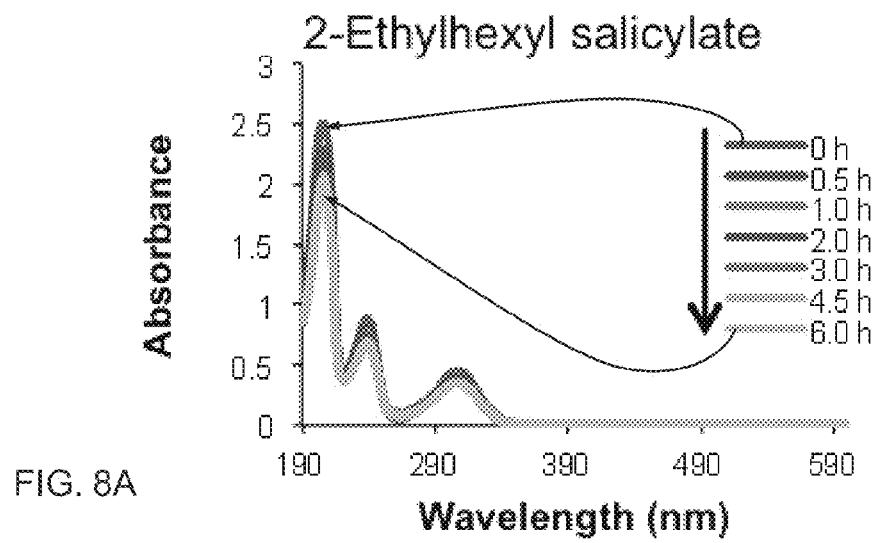
FIGS. 8A-8E show UV-Vis Absorbance spectra for salicylate samples exposed for 6 hours.
Figure 8B:
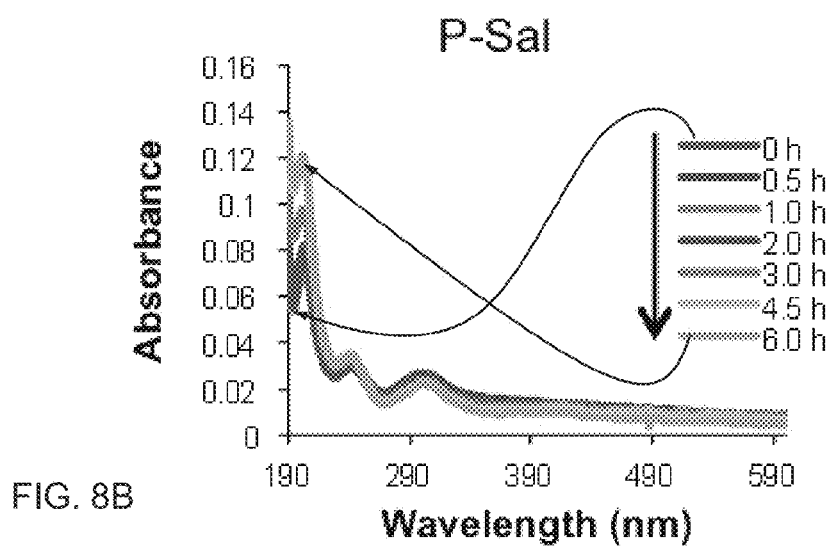
Figure 8C:
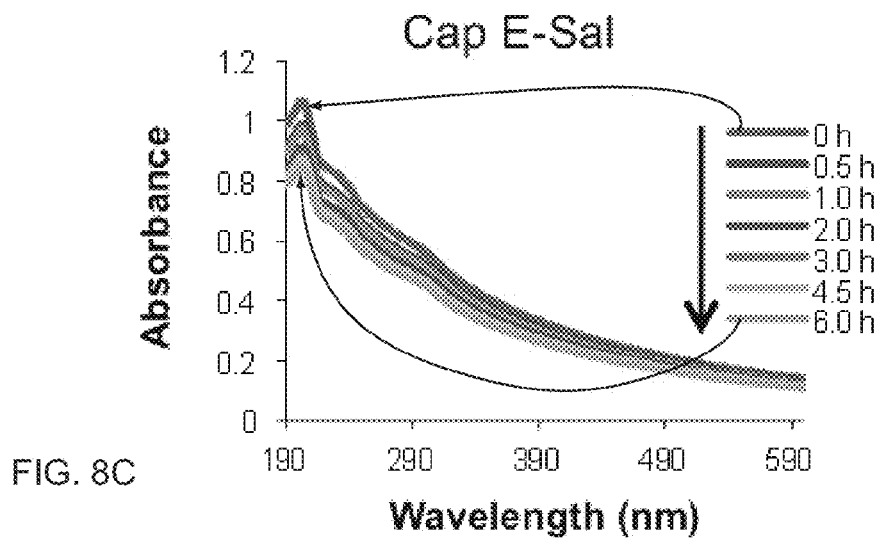
Figure 8D:
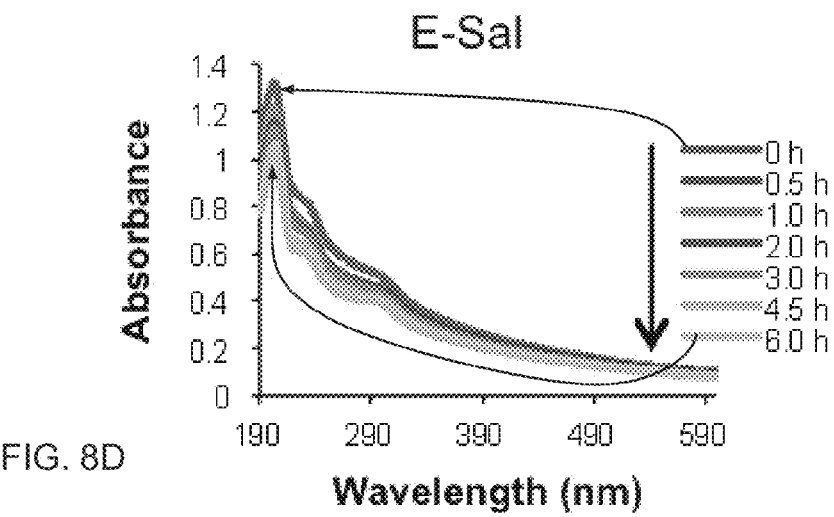
Figure 8E:
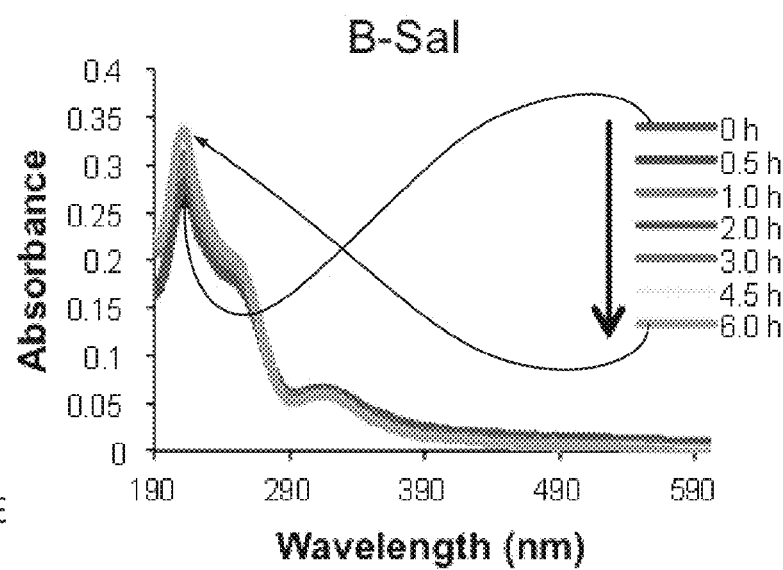
Figure 8F:
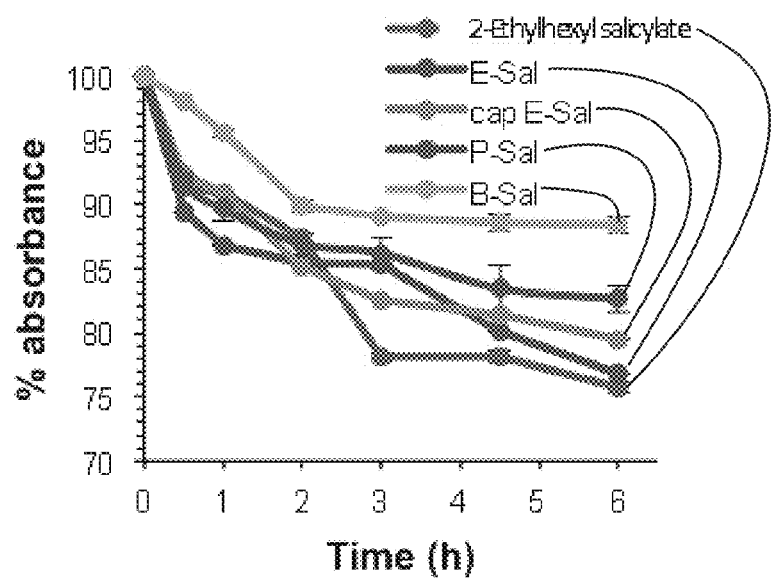
FIG. 8F shows incremental % reduction in UV absorbance at $\lambda_{max}$ (303-315 nm) for each salicylate sample.
Figure 9A:
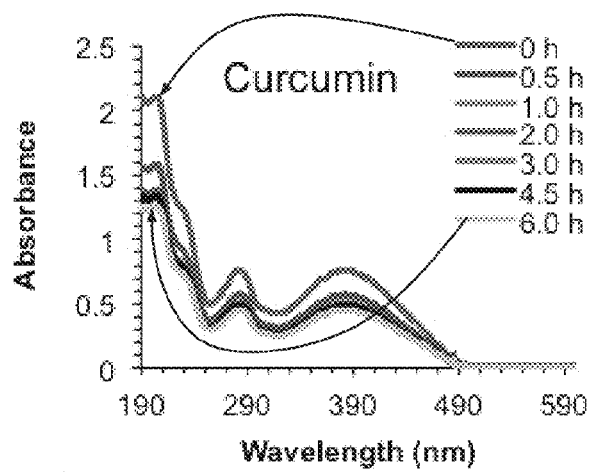
FIGS. 9A-9B show UV-Vis Absorbance spectra for curcuminoid samples exposed for 6 MED, which detail UV-induced degradation over time for each. Incremental % reduction in UV absorbance at $\lambda_{max}$ (382-402 nm) is also shown for each in FIG. 9C.
Figure 9B:
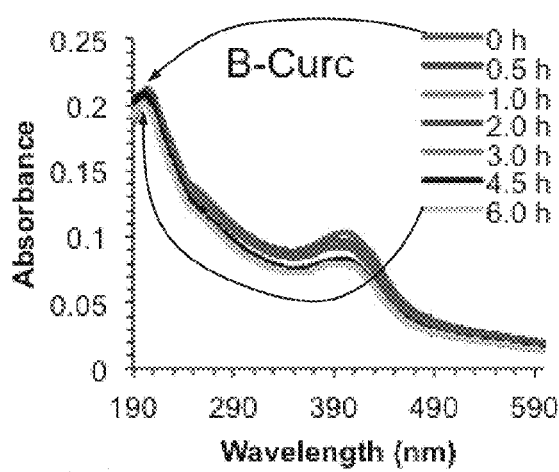
Figure 9C:
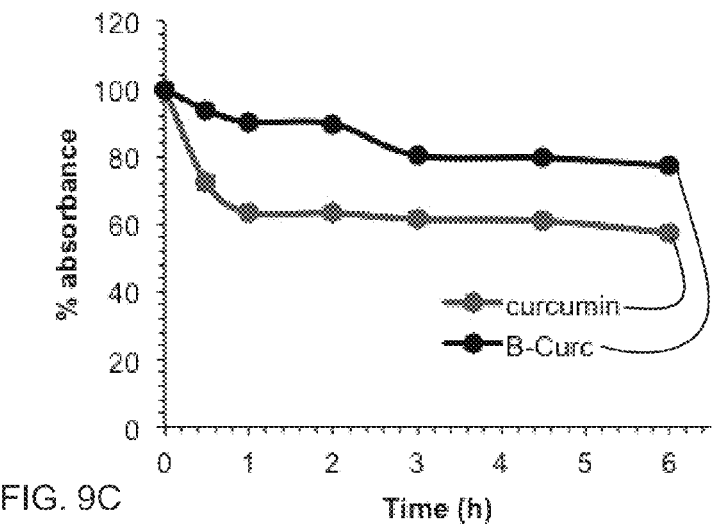

Covalent incorporation of salicylate silsesquioxane analogues 2 (P-Sal) and 4 (B-Sal) was seen to greatly enhance retention, as dye leach out was reduced to 0.80% and 0.04%, respectively. Regarding pendant versus bridged incorporation, more bonds are required to break before the sunscreen can leach from the particle. Of the four samples analyzed, bridged encapsulation was deemed to be the incorporation method of choice due to minimized overall leaching. Based on these results, bridged incorporation is necessary to ensure isolation of sunscreen from skin. This was also evidenced by analysis of the curcuminoid particle sample, for only 0.29% leaching was seen (FIG. 7E).

UV Stability of Incorporated Sunscreen

UV stability of sunscreens is an important criteria in evaluation. Analysis typically involves exposing a sunscreen solution to a specified dosage of UV radiation for a given amount of time, and the effect on spectrophotometric response (typically UV absorbance or fluorescence) is monitored. To adequately simulate the irradiance and dosimetry of natural sunlight exposure, a technique which involves the irradiation of a liquid film sample on glass with a Xenon lamp of a specified irradiance and dosage is used. The effect on UV absorbance before and after exposure is then analyzed.

Essentially, sunscreen particle and liquid sunscreen samples were exposed to UV radiation via a full-spectrum solar simulator (1 sun output intensity), which is designed to mimic the spectrum and intensity of sunlight hitting the earth. The samples were exposed for a total of 6 h at irradiances of 0.039 W/cm$^2$ (UVB) and 0.052 W/cm$^2$ (UVA) per hour. This is equivalent to dosages of 140.4 J/cm$^2$ (UVB) and 187.2 J/cm$^2$ (UVA), or 1.0 MED/h. UV absorbance for each sample was monitored by UV-Vis spectroscopy initially (pre-irradiation) and at specified time intervals. After 6 h, the free sunscreen samples were washed from the quartz slides and photo-products were analyzed by GC-MS or NMR spectroscopy. Summaries of percent UV absorption ability for the irradiated salicylate samples are presented in FIG. 8A-8F and Table 3.

TABLE 3

Summary of sunscreen UV stability data after 6 MED exposure.

| Sample | UV absorption ability after 6 MED exposure* |
|---|---|
| 2-Ethylhexyl salicylate | 75.91 ± 0.26% |
| E-Sal | 76.82 ± 0.01% |
| CapE-Sal | 79.51 ± 0.11% |
| P-Sal | 82.98 ± 0.63% |
| B-Sal | 88.40 ± 0.63% |
| Free curcumin | 57.43 ± 1.66% |
| B-Curc | 77.28 ± 0.09% |

*Data is the summary of three trials.

As expected, the salicylate samples were relatively stable over the course of analysis (a 75%), though UV-induced degradation over time was seen for each (FIG. 8A-8F and Table 3). Comparisons of maximum UV absorbance for each sample (303-315 nm) after 6 MED of exposure detailed that the B-Sal particles retained the highest UV absorption ability at 88.40±0.63%, which is increased over that of free 2-ethylhexyl salicylate (75.74±0.41%) and physically encapsulated 2-ethylhexyl salicylate (76.82±0.01%). Capping of the physically encapsulated 2-ethylhexyl salicylate improved stability (79.51±0.11%), though not as much as that afforded via pendant-covalent incorporation (82.64±1.02%).

The curcuminoid samples were analyzed as above, with B-Curc and free curcumin both displaying UV-induced degradation over time. Attaching the curcumin to the silica particles only shifts the absorption a few nm to slightly longer wavelengths (FIG. 9A-9B) since the attachment during significantly change the electronics of the pi conjugated system. Surprisingly, the present invention has discovered that attaching the curcumin to the B-Curc particles results in a marked increase in UV stability (77.28±0.09%) over that of free curcumin (57.43±1.66%). Free sunscreens were examined after irradiation to give an indication of the photo-degradation pathways, as well as determine plausible structures of photo-products. From these results, the present invention has determined that covalent incorporation is necessary to decrease levels of degradation and isolate any photo-products from skin, and bridged-incorporation is the method of choice to adequately ensure this, thereby achieving long-lasting protection.

In Vitro SPF and UVAPF Determination

In vitro SPF and UVAPF determinations have been developed as fast and reasonable alternatives to in vivo testing due to the eliminated risk of UV exposure to human subjects. For SPF, the most common methods entail measuring UV absorption or transmission of sunscreen films within quartz plates, biomembranes, or synthetic membranes such as 3M Transpore tape.

Using the incremental UV absorbance data from UV stability analysis, SPF values for both salicylate and curcuminoid particles were determined via the methodologies known in the arts and in accordance with Cosmetics Europe (COLIPA) protocols, which involve measuring the transmittance of a given sunscreen sample across the UVB spectrum (290-320 nm) weighted against the erythemal effect and solar intensity at each wavelength, as defined by Equation 1:

$$SPF_{in\ vitro} = \frac{1}{T} = \frac{\sum_{290}^{320} EE(\lambda) * I(\lambda)}{\sum_{290}^{320} EE(\lambda) * I(\lambda) * T(\lambda)} \quad \text{Equation 1}$$

where EE is the erythemal effect spectrum, I is the solar intensity spectrum, and T is the sunscreen transmittance. The normalized values of EE*I (shown in Table C), which are constants measured in 5 nm increments, define a sunscreen which transmits all light as having an SPF of 1.0, while one that absorbs all light as having an SPF of infinity.

TABLE C

Normalized product function used to calculate SPF, where EE = erythemal effect spectrum and I = solar intensity spectrum (57).

| Wavelength (nm) | EE*I |
|---|---|
| 290 | 0.0150 |
| 295 | 0.0817 |
| 300 | 0.2874 |
| 305 | 0.3278 |
| 310 | 0.1864 |
| 315 | 0.0839 |
| 320 | 0.0180 |
| Total | 1 |

Equation 1 was further derived to improve method standardization by incorporating a correction factor, CF (Equation 2):

$$SPF_{in\ vitro} = CF * \sum_{290}^{320} \left(\frac{EE(\lambda) * I(\lambda)}{T(\lambda)}\right)$$

$$= CF * \sum_{290}^{320} EE(\lambda) * I(\lambda) * Abs(\lambda)$$

Equation 2 where Abs is the sunscreen absorbance, and CF=10 so that a standard 8% homosalate sunscreen would calculate to an SPF of 4.

Figure 10:
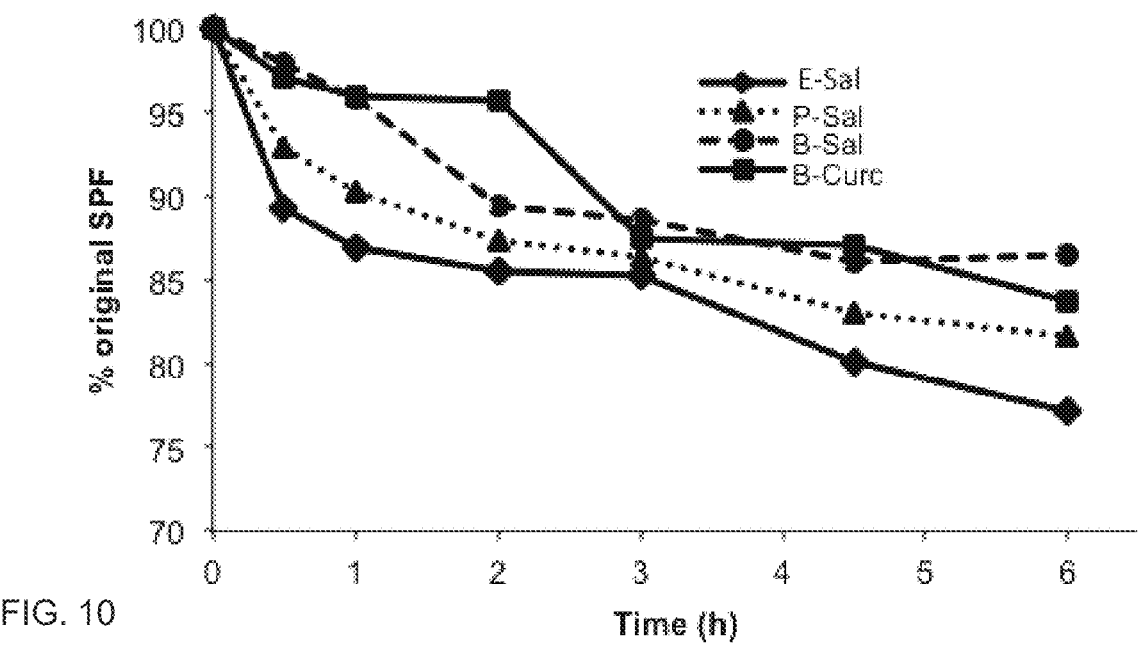
FIG. 10 shows incremental SPF reduction for salicylate and curcuminoid particles after UV irradiation over time.

Calculated SPF values for the un-irradiated particle samples are presented in Table 4. The salicylate values are relatively low when taking into account typical SPFs of commercial sunscreens, which would explain why other UVB absorbers in addition to salicylate ingredients are included within commercial formulations. This is likely due to the low molar extinction coefficient (4900 $M^{-1}$ $cm^{-1}$ for 2-ethylhexyl salicylate), which arises from steric strain and slight deviation from planarity due to the ortho configuration of the hydroxyl and carboxylate residues. It is also important to remember that only small amounts of sunscreen (less than the theoretical 1.0 mole %) are incorporated for each sample (Table 2). Regarding physical versus covalent SPFs, a bathochromic shift in pre-irradiated UV absorbance was seen for the P-Sal and B-Sal samples (which contain incorporated salicylate silsesquloxanes) from that of E-Sal, which contains 2-ethylhexyl salicylate encapsulated within (FIG. 10). This would imply a reduced ability to absorb UVB radiation, resulting in a lower SPF.

TABLE 4

Summary of in vitro SPF data for salicylate and curcuminoid particles before and after UV exposure.

| Sample | SPF* | % SPF maintained after 0.5 MED exposure | % SPF maintained after 6.0 MED exposure |
|---|---|---|---|
| E-Sal | 3.72 | 89.23 | 77.13 |
| P-Sal | 0.21 | 92.87 | 81.63 |
| B-Sal | 0.55 | 97.98 | 86.53 |
| B-Curc | 0.85 | 97.06 | 83.74 |

*Calculated from Equation 2

More interesting, however, is the incremental SPF values after UV irradiation for each sample (FIG. 10 and Table 4). After just 0.5 MED of exposure, SPF of the E-Sal particles was reduced by 10.8%, which is greater than that experienced by P-Sal (7.1%) and B-Sal (2.0%) particles. B-Curc particles experienced a comparable reduction of 3.0%. By 6 MED, the SPF of B-Sal was still only reduced by 13.5%, while the E-Sal and P-Sal samples display reductions of 22.9% and 18.4%, respectively. As before, the B-Curc particles also maintained SPF well, with only 16.3% reduction seen. Without wishing to limit the invention to a particular theory or mechanism, this maintenance of SPF can be attributed to the increased UV stability achieved with bridged incorporation, as the calculation correlates with the UV absorption ability over time.

Since salicylates and curcuminoids also absorb UVA radiation, UVAPF, which delineates the efficacy of UVA protection, was also calculated for these samples. Similar to SPF, UVAPF compares the minimum UVA dosage necessary to produce immediate or persistent pigment darkening (PD) with and without sunscreen. In vitro UVAPF determination is inherent with cross-laboratory variability such as substrate interactions, sunscreen film uniformity, sunscreen fluorescence, and sunscreen UV absorbance. To address these concerns, several methods have been developed that entail evaluating the breadth of UVA protection in comparison with UVB instead of absolute absorbance measurements. Two such methods were utilized in this study: the FDA recommended Critical Wavelength Method, and the UK Boot's Method.

The Critical Wavelength Method involves integrating the broad spectrum (290 nm-400 nm) absorbance of a sunscreen film until the sum reaches 90% of the total area under the curve of this region. The wavelength that corresponds to this 90% sum is defined as the critical wavelength, and must lie between 290 nm-320 nm for the sunscreen to provide appreciable UVB protection. The critical wavelength must be at least 370 nm for the sunscreen to be defined as broad-spectrum (UVA UVB). The critical wavelength is defined according to Equation 3:

$$\int_{290}^{\lambda_c} A(\lambda)d\lambda = 0.9\int_{290}^{400} A(\lambda)d\lambda$$

Equation 3 where $\lambda_c$ is the critical wavelength, $A(\lambda)$ is the average absorbance at each wavelength, and $d\lambda$ is the wavelength interval between measurements. Critical wavelengths for each sunscreen particle sample are >370 nm (Table 5), implying none provide adequate UVB protection, as expected. However, they can still be classified as broad-spectrum. The salicylate values are red-shifted from that of free 2-ethylhexyl salicylate at 331 nm.

TABLE 5

Critical Wavelength of salicylate and curcuminoid particles.

| Sample | Critical Wavelength (nm)* |
|---|---|
| E-Sal | 384 |
| P-Sal | 384 |
| B-Sal | 379 |
| B-Curc | 389 |

*Calculated from Equation 3

The Boots Method also involves measuring the integrated broad-spectrum UV absorbance of a sunscreen film before and after exposure to a controlled dose of UV radiation from a defined source. This data is then used to calculate UVA/UVB absorbance ratios according to Equations 4 and 5:

$$UVA/UVB\ ratio_0 = \frac{\int_{320}^{400} A_0(\lambda)d\lambda \Big/ \int_{320}^{400} d\lambda}{\int_{290}^{320} A_0(\lambda)d\lambda \Big/ \int_{290}^{320} d\lambda}$$

Equation 4

$$UVA/UVB\ ratio = \frac{\int_{320}^{400} A(\lambda)d\lambda \Big/ \int_{320}^{400} d\lambda}{\int_{290}^{320} A(\lambda)d\lambda \Big/ \int_{290}^{320} d\lambda}$$

Equation 5 where $A_0(\lambda)$ is the mean absorbance before UV exposure, $A(\lambda)$ is the mean absorbance after UV exposure, and $d\lambda$ is the incremental wavelength (1 nm). The closer each ratio is to unity, the higher the level of UVA protection. These pre- and post-irradiation ratios are then compared and utilized to classify the sunscreen into the five categories (or star levels) of protection of the Boots Star Rating System. Like SPF determination, UV stability absorbance data was utilized for all UVAPF calculations. Summaries of UVAPF data are presented in Table 6.

TABLE 6

UVA/UVB ratios and Boot's Star Ratings for salicylate and curcuminoid particles.

| Sample | UVA/UVB Ratio* | Boot's Star Rating | UVA/UVB Ratio (6 MED)@ | Boot's Star Rating (6 MED) |
|---|---|---|---|---|
| E-Sal | 0.66 | ***(Good) | 0.65 | ***(Good) |
| P-Sal | 0.65 | ***(Good) | 0.53 | **(Moderate) |
| B-Sal | 0.62 | ***(Good) | 0.54 | **(Moderate) |
| B-Curc | 0.93 | *****(Ultra) | 0.90 | ****(Superior) |

*Calculated from Equation 4;
@Calculated from Equation 5

Analysis of the pre-irradiation UVA/UVB ratios details all salicylate samples are adequate UVA absorbers, with Boot Star Ratings of 3 stars for each. The curcuminoid particles rate "Ultra" for UVA protection with 5 stars. This pre-irradiation UVA protective ability directly correlates with UV absorbance profiles of the parent compounds, as curcuminoids absorb more strongly in the UVA region than salicylates. The E-Sal UVA/UVB ratio was un-affected after 6 MED, for the Boots Star Rating was maintained at "good". Unfortunately, irradiation with 6 MED seems to affect UVA absorption ability for the P-Sal and B-Sal particles the most, as illustrated by an increased hypsochromic shifts in UV absorbance over that of E-Sal, resulting in reduced UVA/UVB ratios. This was enough to reduce the Boot's Star Rating by one star from "good" to "moderate" for each. The B-Curc particles were comparable to the covalent salicylate particles, with a rating reduction from "ultra" to "superior".

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A sunscreen composition comprising one or more monomers of a bridged compound according to Formula I:

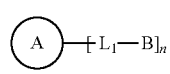

Formula I wherein A is a UV absorbing moiety, wherein A is selected from a group consisting of salicylate, curcuminoid, benzophenone, acetophenone, and cinnamate monomers,
wherein $L_1$ is a linker group according to Formula II, III, or IV:

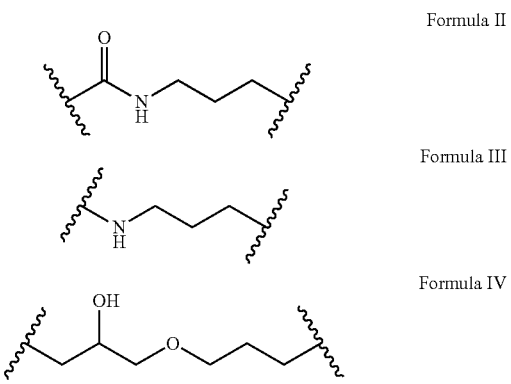

wherein B is a trialkoxysilyl group,
wherein n is at least 2,
wherein $L_1$ is covalently bonded to A to effectively prevent leeching of A from the sunscreen composition, wherein the multiple trialkoxysilyl groups of the bridged compound monomers are polymerized with tetraalkoxysilane comonomers to form bridged polysilsesquioxane-based sunscreen particles, and wherein the sunscreen composition is resistant to photo-degradation.

2. The sunscreen composition of claim 1, wherein A comprises at least two functional groups selected from a group consisting of a hydroxyl, an amine, and a carboxylic acid moiety, wherein $L_1$ is covalently bonded to the functional group.

3. The sunscreen composition according to claim 1, wherein the trialkoxysilyl group is a triethoxysilyl group or trimethoxysilyl group.

4. The sunscreen composition according to claim 1, further comprising silicate comonomers in concentrations ranging from 0.001-95 mole %, wherein the silicate comonomers are copolymerized with the bridged compound monomers to form the bridged polysilsesquioxane-based sunscreen particles.

5. The sunscreen composition of claim 4, wherein the silicate comonomers are selected from a group consisting of tetraalkoxysilane comonomers, sodium silicate comonomers, and organotrialkoxysilane comonomers.

6. The sunscreen composition of claim 5, wherein the tetraalkoxysilane comonomers are selected from a group consisting of tetramethoxysilane comonomers and tetraethoxysilane comonomers.

7. The sunscreen composition according to claim 1, wherein each sunscreen particle has a mean diameter of about 50 to 750 nm.

8. The sunscreen composition according to claim 1, wherein the sunscreen composition is prepared by sol gel polymerization, microemulsion polymerization, or modified Stober polymerization.

9. A sunscreen formulation comprising:
a. the sunscreen composition according to claim 1, wherein the sunscreen composition is present in an amount effective to absorb UV radiation; and
b. a pharmaceutically-acceptable sunscreen carrier.

10. A sunscreen composition comprising one or more monomers of a bridged compound according to Formula I:

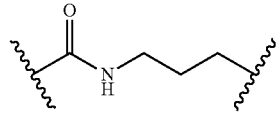

Formula I wherein A is a UV absorbing moiety, wherein A is selected from a group consisting of salicylate; curcuminoid, benzophenone, acetophenone, and cinnamate monomers, wherein $L_1$ is a linker group according to Formula II, III, or IV:

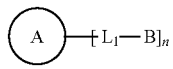

Formula II

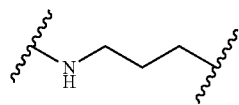

Formula III

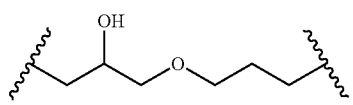

Formula IV wherein B is a trialkoxysilyl group,
wherein n is at least 2,
wherein $L_1$ is covalently bonded to A to effectively prevent leeching of A from the sunscreen composition, wherein the multiple trialkoxysilyl groups of the bridged compound monomers are reacted with tetrafunctional comonomers to form bridged polysilsesquioxane-based sunscreen particles, and wherein the sunscreen composition is resistant to photo-degradation.

* * * * *